US005507717A

United States Patent [19]
Kura et al.

[11] Patent Number: 5,507,717
[45] Date of Patent: Apr. 16, 1996

[54] DEVICE FOR BENDING THE INSERTION SECTION OF AN ENDOSCOPE

[75] Inventors: Yasuhito Kura; Takayuki Yokota; Koji Nakamoto; Masaaki Nakazawa; Hisao Yabe; Hideo Ito, all of Tokyo, Japan

[73] Assignee: Olympus Optical Co., Ltd., Tokyo, Japan

[21] Appl. No.: 248,422

[22] Filed: May 24, 1994

[30] Foreign Application Priority Data

May 24, 1993 [JP] Japan ................................. 5-121603
Dec. 28, 1993 [JP] Japan ................................. 5-354158

[51] Int. Cl.$^6$ ........................................................ A61B 1/00
[52] U.S. Cl. ........................................................ 600/146
[58] Field of Search ........................ 128/4–10; 600/146

[56] References Cited

U.S. PATENT DOCUMENTS 4,742,816  5/1988  Suzuki et al. ............................ 128/4

Primary Examiner—Richard J. Apley
Assistant Examiner—John P. Leubecker
Attorney, Agent, or Firm—Frishauf, Holtz, Goodman, Langer & Chick

[57] ABSTRACT

A device to be incorporated in the housing of the operation section of an endoscope, for operating a bending mechanism incorporated in the insertion section of the endoscope, comprises an operation shaft and a holder. The operation shaft has a distal end connected to the bending mechanism and a proximal end portion projecting from an operation section of the endoscope. The holder is mounted on a distal end portion of the operation shaft and comprises an upper and lower cover which are joined together and which define an outside surface and a hollow cylindrical space around the operation shaft. The upper and lower covers abut each other to form an interface on the outside surface.

23 Claims, 21 Drawing Sheets

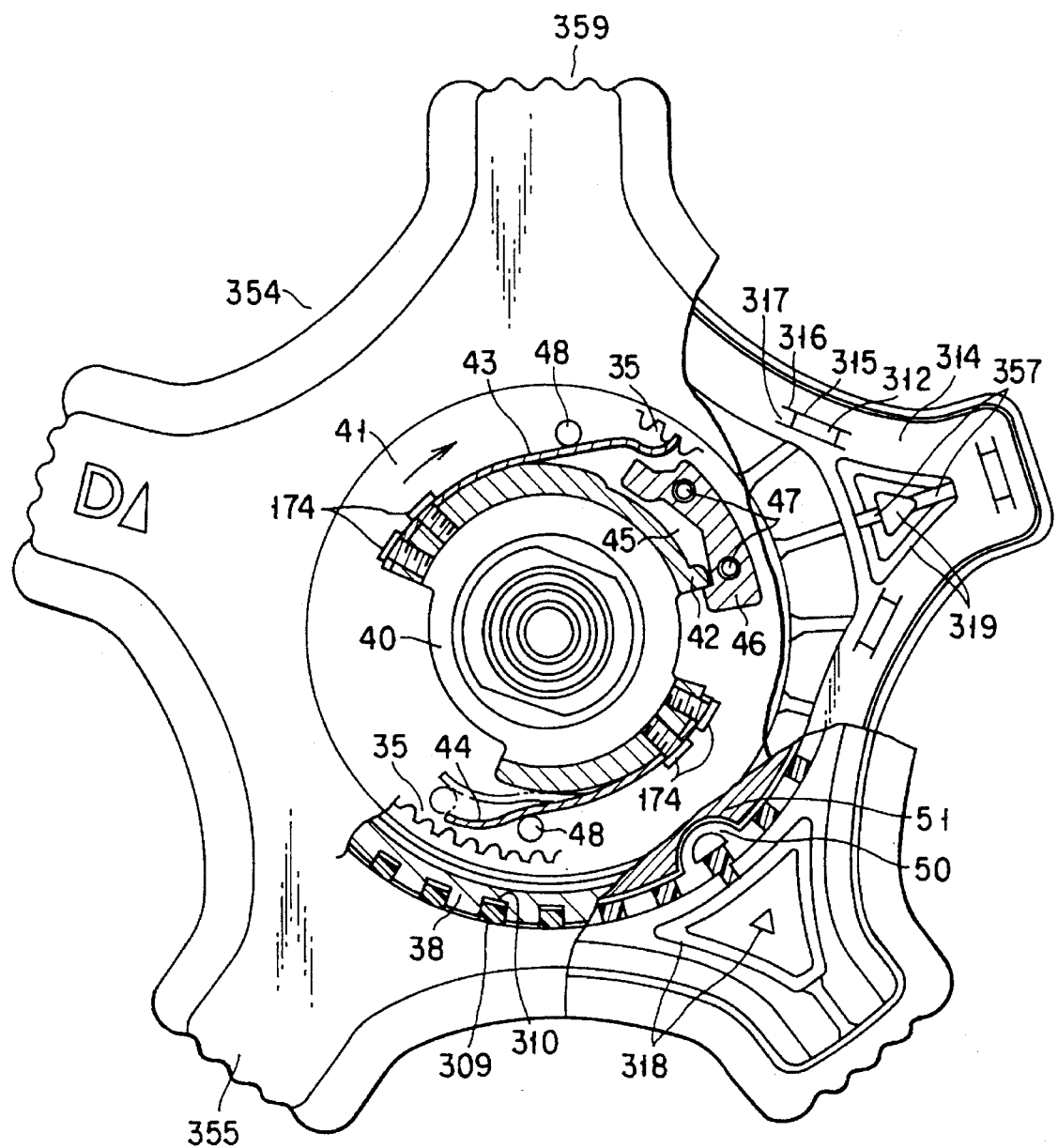
F I G. 14

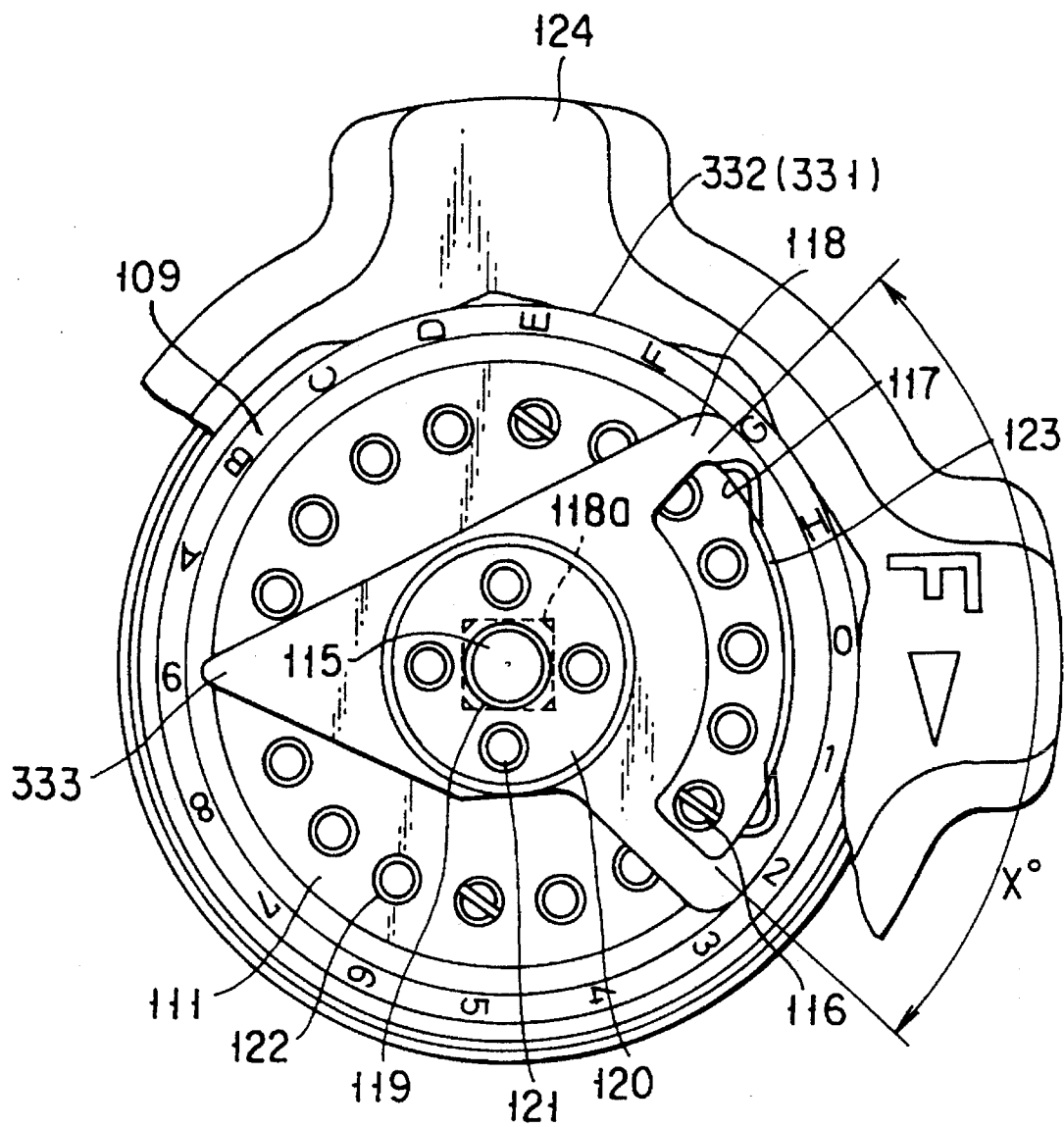
F I G. 16

DEVICE FOR BENDING THE INSERTION SECTION OF AN ENDOSCOPE

BACKGROUND OF THE INVENTION

1. Field of the Invention

The present invention relates to a device for bending the insertion section of an endoscope, by remote control performed at the operation section of the endoscope.

2. Description of the Related Art

As disclosed in Jpn. UM Appln. KOKOKU Publication No. 63-9292, a device for bending the insertion section of an endoscope comprises an operation member and an operation knob. The operation member is a hollow cylinder which is rotatably mounted on a fixed shaft of an endoscope. The operation knob is connected to one end of the operation member. The other end of the operation member is connected to the bending mechanism incorporated in the insertion section of the endoscope. When the operation knob is rotated, the operation member is driven, actuating the bending mechanism. When actuated, the bending mechanism bends the insertion section of the endoscope.

Most devices of this type further comprise a brake mechanism which is located near the operation knob and which is designed to maintain the insertion section in a bent state and to minutely change the bent state of the insertion section. The operation knob, the brake mechanism and the operation member (a hollow cylinder) are connected to one another by connectors. The connectors are exposed at the top and side of the operation knob. The connectors are fitted, in part, in the recesses made in some components of the bending device.

Dust and dirt are likely to accumulate at the connectors and in the recesses in which the connectors are fitted. Once dirt has so accumulated, it would take much time and labor to wash the dust and dirt away from the connectors and the recesses. After the washing, the cleaning water stays in the recesses, and it usually takes much time and labor to remove the water from the recesses.

Not only is it necessary to take measures to facilitate the washing of the device. But also is it required that the operability of the device be improved by, for example, making the operation knob lighter so that the knob may be easily rotated by hand.

SUMMARY OF THE INVENTION

The object of the present invention is to provide a device for bending the insertion section of an endoscope, which can be easily washed and which is light and easy to operate.

To attain the object, according to the invention there is provided a device to be incorporated in the housing of the operation section of an endoscope, for operating a bending mechanism incorporated in the insertion section of the endoscope, the device comprising: an operation shaft having a distal end connected to the bending mechanism and a proximal end portion projecting from an operation section of the endoscope; and holder means mounted on distal end portion of the operation shaft and comprising a plurality of covers which are joined together and which define a space around the operation shaft.

Since the holder means is a hollow member, it is relatively light and easy to operate. The holder means comprises an upper cover and a lower cover, which abut on each other, forming a seam. Each cover has a smooth and continuous outer surface each, and the seam has a surface continuous to the outer surface of each cover. Therefore, the holder means has no recesses in its outer surface, in which dust and dirt may accumulate, and the holder means is easy to wash and clean.

The upper cover and the lower cover may be connected such that the seam is located on the lower surface of the holder means. In this case, dust or dirt is unlikely to enter the holder means through the seam, and the outer surface of the upper cover can easily be cleaned with alcohol-moistened gauze or the like. It is sufficient if the upper cover only has a smooth upper surface and a smooth circumferential surface.

Alternatively, the upper cover and the lower cover may be connected such that the seam is located on the upper or circumferential surface of the holder means. If this is the case, dust or dirt, if accumulated at the seam, is conspicuous and can be removed with ease.

Various mechanisms may be contained in the holder means. In a preferred embodiment of the invention, a brake mechanism for applying a brake on the operation shaft and some other mechanisms are located in the holder means. The interface between the upper and lower covers is sealed watertight so that washing water may not flow into the holder means. Since the holder means contains almost all other components of the device and has a smooth outer surface, much time or labor is required to wash the device.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 14 is a partly sectional plan view of the first bending unit of the bending device;

FIG. 16 is a partly sectional view showing the internal structure of the third bending unit of the bending device;

DETAILED DESCRIPTION OF THE PREFERRED EMBODIMENTS

An embodiment of the present invention will be described, with reference to the accompanying drawings.

Figure 1:
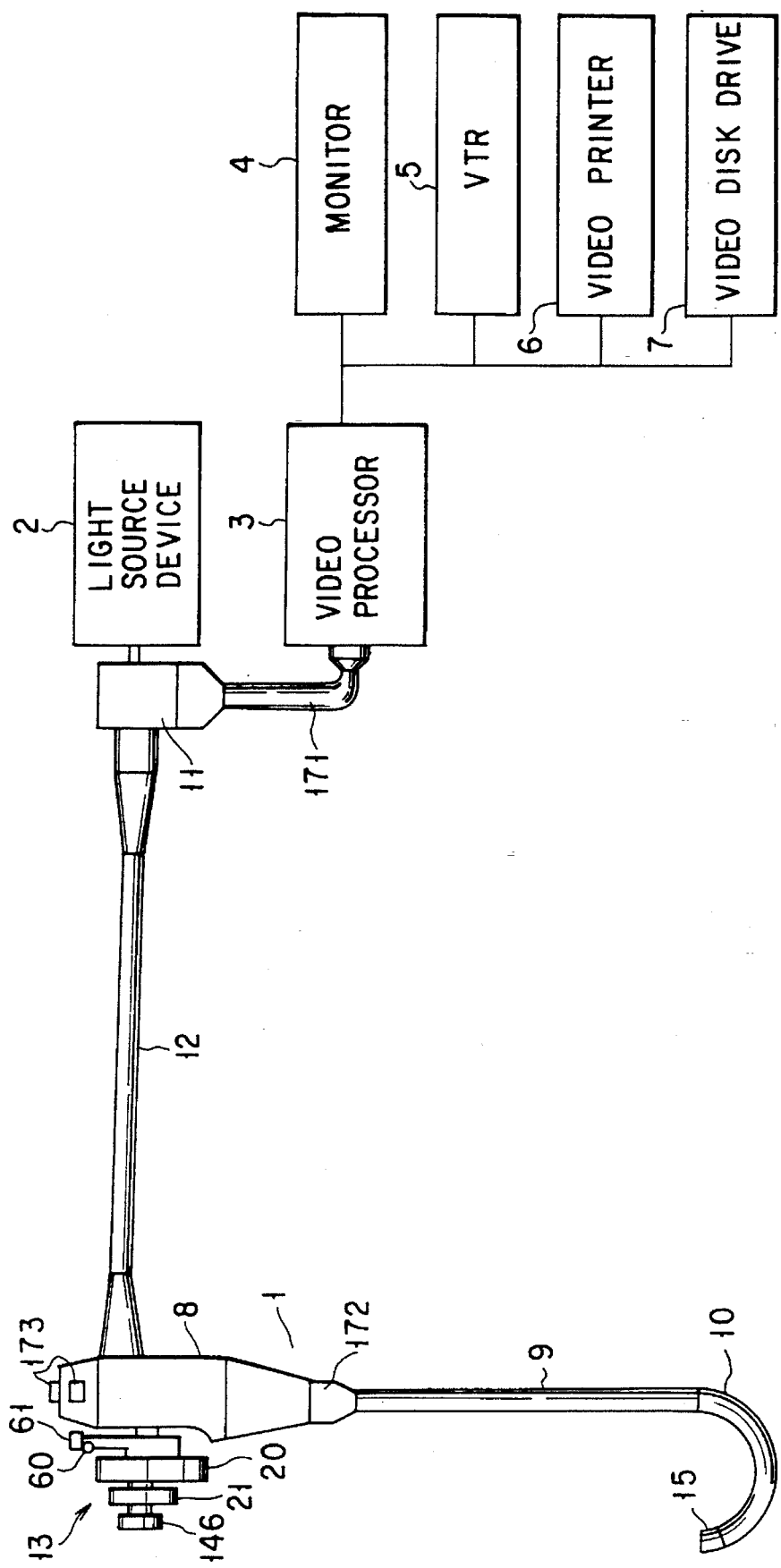
FIG. 1 is a diagram schematically showing an electronic endoscope system.

Shown in FIG. 1 is an electronic endoscope system which incorporates the embodiment of the invention. The electronic endoscope system comprises an electronic endoscope 1, a light source device 2, a video processor 3, a monitor television (TV) 4, a video tape recorder (VTR) 5, a video printer 6, and a video disk drive 7. The endoscope 1 is used to observe the interior of a body cavity and perform various treatments in the body cavity. The light source device 2 is coupled to the endoscope 1, for applying illumination light via the endoscope 1 into the body cavity. The video processor 3 is electrically connected to the endoscope 1, for processing optical signals output from the endoscope 1 and generating video signals from the optical signals. The monitor TV 4, the VTR 5, the video printer 6 and the video disk drive 7 are connected to the video processor 3. The monitor TV 4 is designed to display an image of an object present in the body cavity, the VTR 5 to record the video signals on magnetic tape and reproducing the video signals therefrom, the video printer 6 to print the image on a recording paper sheet, and the video disk drive 7 to record the video signals. The video disk drive 7 has a data-storage capacity far greater than the VTR 5.

The electronic endoscope 1 comprises an operation section 8 and an insertion section 9 connected to the operation section 8. Mounted on the node of the sections 8 and 9 is a cylindrical reinforcing member 172, which prevents the proximal end portion of the insertion section 9 from being bend and broken. The insertion section 9 comprises a rigid tube connected to the operation section 8, a flexible tube 10 connected to the distal end of the rigid tube, and a distal end unit 15 coupled to the distal end of the flexible tube 10. The distal end unit 15 contains various optical components which constitute a photographing optical system, an illumination system and the like. A universal chord 12 is connected at one end to the operation section 8 by a connector, and at the other end to the light source device 2 by a connector 11. The universal cord 12 which contains a light guide and a signal cable. The connector 11 is connected to the video processor 3 by a scope cable 171. Hence, the electronic endoscope 1 is connected to the light source device 2 and the video processor 3.

A bending device 13, which is an embodiment of the present invention, is coupled to the operation section 8 of the electronic endoscope 1. When operated by an operator, the device 13 actuates the bending mechanism (later described) provided in the flexible tube 10, thereby to bend the flexible tube 10 and moving the distal end unit 15 up and down, from the left to the right, and vice versa. A plurality of switches 173 are mounted on the distal end of the operation section 8. The switches 173 may be selectively operated to remote-control the video processor 3.

Figure 2:
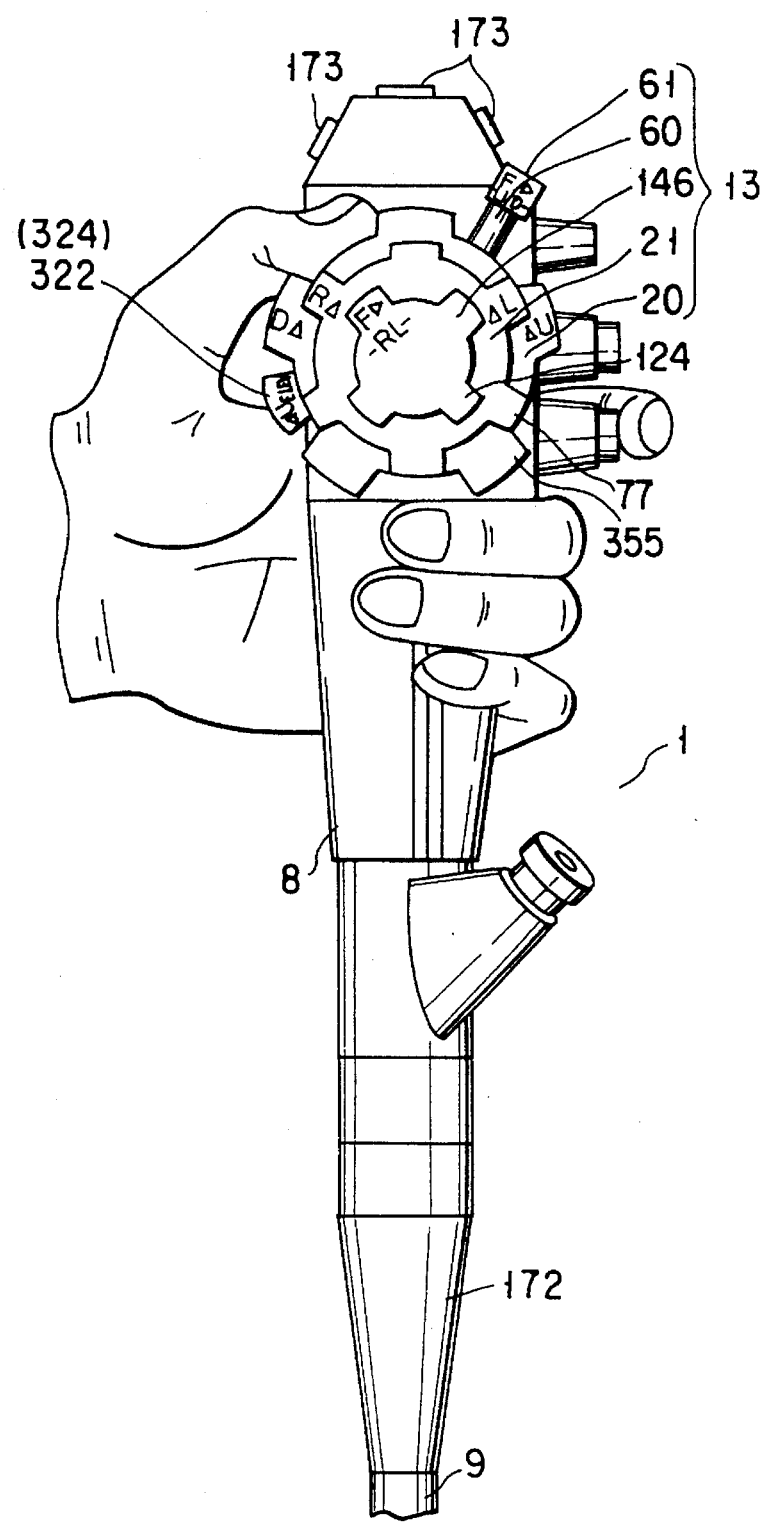
FIG. 2 is a side view of the operation section of the electronic endoscope shown in FIG. 1.

The electronic endoscope 1 has a forceps holder (not shown), an operation wire (not shown), and a forceps-driving unit 324 (FIG. 2). The forceps holder is rotatably connected to the distal end of the rigid tube of the insertion section 9. The operation wire is connected at one end to the forceps holder and at the other end to the forceps-driving unit 324. When the unit 324 is rotated in one direction, it pulls the wire to rotate the forceps holder such that the forceps held by the holder is held up.

The bending mechanism, the bending device 13, and the forceps-driving unit 324 will be described in more detail.

Figure 3:
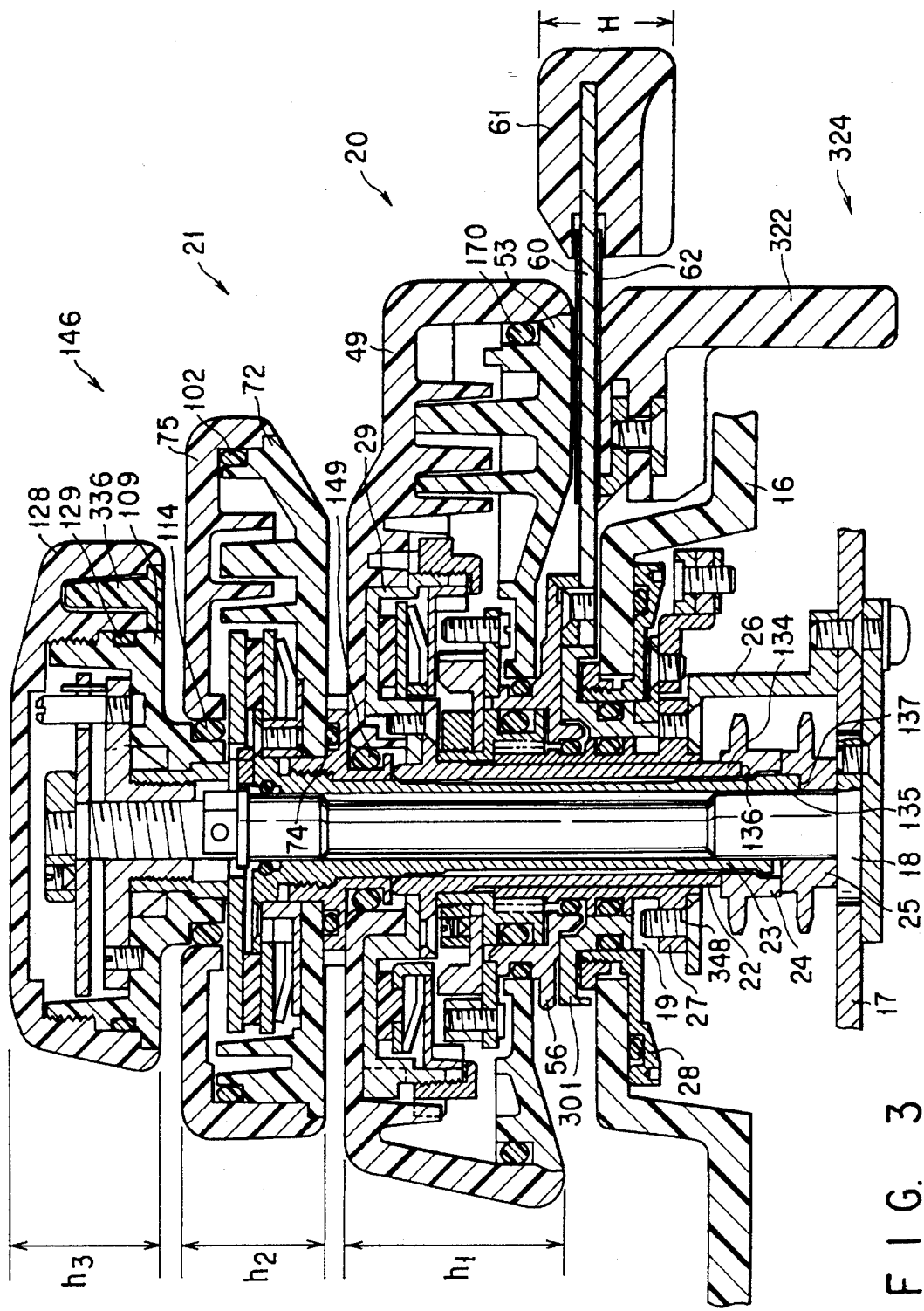
FIG. 3 is a side sectional view of the bending device connected to the electronic endoscope.

As shown in FIG. 3, a base plate 17 is secured to the housing 16 of the operation section 8. A fixed shaft 18 is fastened to the base plate 17. More specifically, one end portion of the shaft 18 is set in screw engagement with the base plate 17. The other end portion of the shaft 18 projects outwards from the operation section 8 through a hole 19 made in the housing 16.

Three bending units 20, 21 and 146 are mounted on the fixed shaft 18 and located one above the other in coaxial alignment. To be more specific, the first bending unit 20 the second bending unit 21 is mounted on a first sleeve 22 which is mounted on a second sleeve 23, and the second bending unit 21 is mounted on the second sleeve 23 which is mounted on the fixed shaft 18. Each of the bending units 20, 21 and 146 has a rotatable holder and various mechanisms including a brake mechanism (later described). The holder comprises an upper cover and a lower cover connected to the upper cover. The mechanisms are contained in the holder. The upper cover is an operation knob. The operation knob of any bending unit is spaced apart from the lower cover of the holder of the bending unit located immediately above that bending unit.

A first sprocket 24 is fastened to that end portion of the first sleeve 22 which is located in the operation section 8. Similarly, a second sprocket 25 is fastened to that end portion of the second sleeve 23 which is located in the operation section 8. The first sprocket 24 has an engagement groove 136, and the second sprocket 25 has an engagement groove 137. The first sleeve 22 has a claw 134, and the second sleeve 23 a claw 135. The claw 134 of the first sleeve 22 is fitted in the engagement groove 136 of the first sprocket 24, which will therefore be rotated when the first sleeve 22 is rotated. The claw 135 of the second sleeve 23 is fitted in the engagement groove 137 of the second sprocket 25, which will therefore be rotated when the second sleeve 23 is rotated.

First and second chains (not shown) are wrapped around and set in mesh with the first sprocket 24 and the second sprocket 25, respectively. Two operation wires are connected to the ends of each chain. The first sprocket 24 is so located that the claw 134 fits in the engagement groove 136 of the first sprocket 24 when the first operation knob 49 of the first bending unit 20 assumes a neutral position. The second sprocket 25 is so located that the claw 135 fits in the engagement groove 137 of the second sprocket 25 when the second operation knob 75 of the second bending unit 21 assumes a neutral position.

The first chain is so located that the nodes of this chain and the two operation wires are positioned at the same distance from the first sprocket 24 when the operation knob 49 of the first bending unit 20 assumes a neutral position. Similarly, the second chain is so located that the nodes of the chain and the two operation wires are positioned at the same distance from the second sprocket 25 when the operation knob 75 of the second bending unit 21 assumes a neutral position.

Two segments (not shown) are provided in the flexible tube 10 and secured to the inner surface thereof. The two operation wires extending from the first chain are connected to the first segment, at first and second points on the circumference of the first segment which are diametrically opposite to each other. On the other hand, the two operation wires extending from the first chain are connected to the second segment, at third and fourth points on the circumference of the second segment which are diametrically opposite to each other and which are spaced by 90° from the first and second points, respectively. When the first sprocket 24 is rotated, the operation wires connected to the sprocket 24 are pulled and slackened, respectively, the first segment is tilted, bending the flexible tube 10 upward or downward. When the second sprocket 25 is rotated, the operation wires connected to the sprocket 25 are pulled and slackened, respectively, the second segment is tilted, bending the flexible tube 10 to the left or the right.

Figure 4:
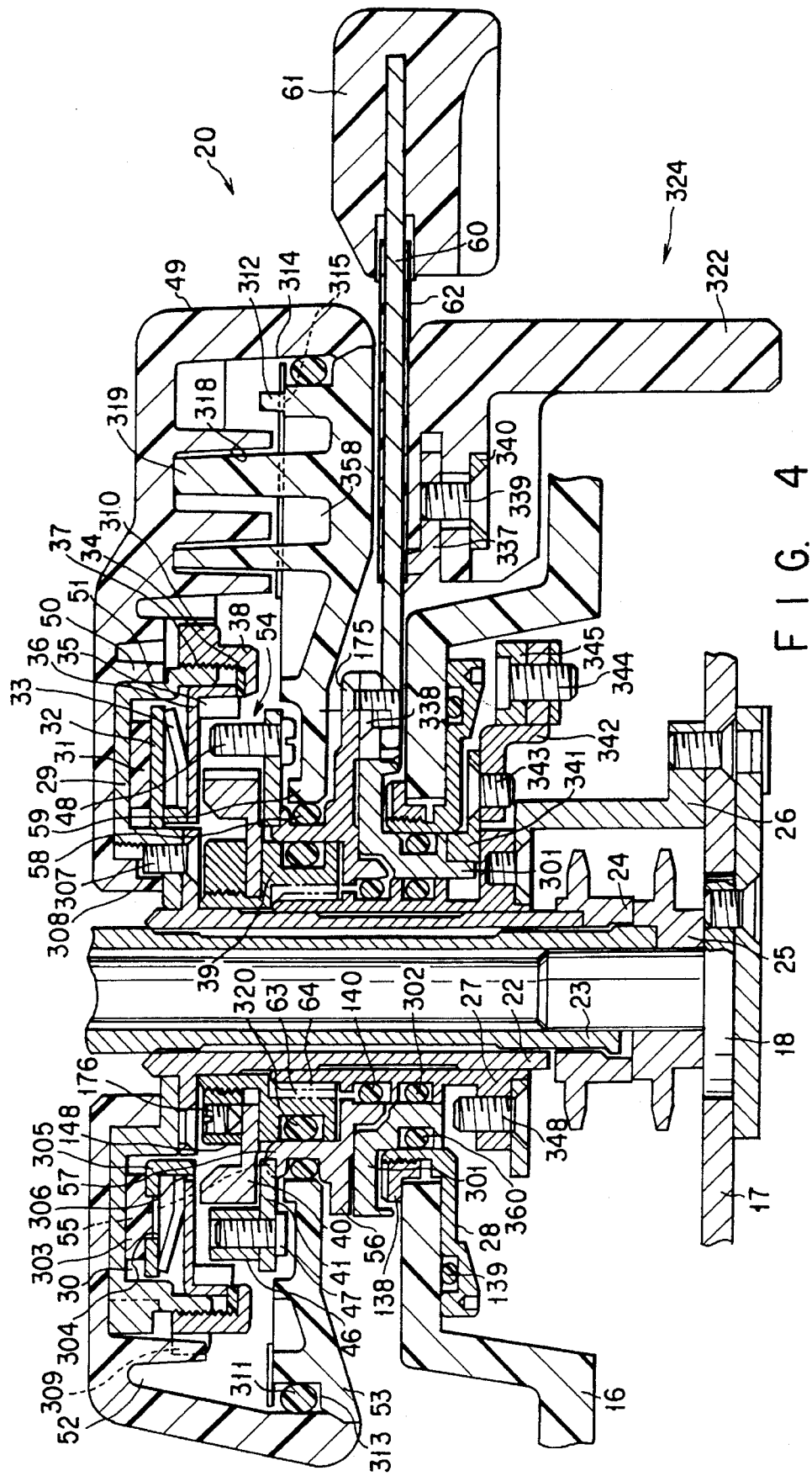
FIG. 4 is a side sectional view of the first bending unit of the bending device illustrated in FIG. 3.

The base plate 17 is covered by a cover 26. A bearing 27 is fastened at one end to the cover 26 and located in the hole 19 of the housing 16. Fitted in the bearing 27 is the first sleeve 22, in which the second sleeve 23 is fitted. A ring 301 is rotatably mounted on the bearing 27. As shown in FIG. 4, the ring 301 is supported by a support shaft 28 which is set in screw engagement with a fastener 138 and which is thereby fastened to the housing 16. A first O-ring 139 is interposed between the housing 16 and the support shaft 28, forming a watertight seal. A second O-ring 140 is mounted on the bearing 27, forming a watertight seal between the bearing 27 and a brake plate 56. Furthermore, a third O-ring 302 is mounted on the bearing 27, forming a watertight seal between the bearing 27 and the ring 301.

The first bending unit 20 will be described, with reference to FIG. 4.

Figure 17:
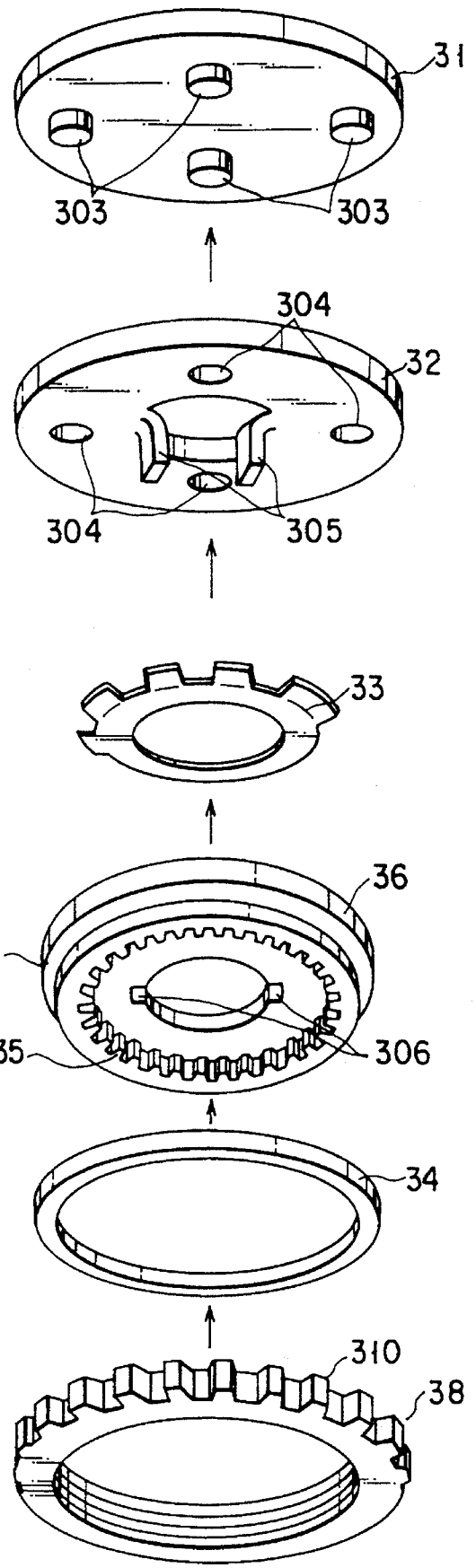
FIG. 17 is an exploded view of the first bending unit, explaining how the unit has been assembled.

A first receptacle 29, which is the uppermost component arranged within the first bending unit 20, is fastened by at least one screw 307 to the flange which is formed integral with the upper end of the first sleeve 22. The first receptacle 29 defines an annular chamber 30. In the chamber 30, a first friction plate 31 is secured to the upper surface of a first friction member 32. The first friction member 32 is biased upwards by a first shaped leaf spring 33. The first friction member 32 is mounted on the inner periphery of the first receptacle 29. The first leaf spring 33 is mounted on a first support plate 36 which has splines 35 on the inner periphery. The first friction plate 31, the first friction member 32, the first leaf spring 33 and the first support plate 36 are held in the annular chamber 30 by an annular holder 38, as is illustrated in FIG. 17 The annular holder 38 has a threaded inner periphery 37 which is set in screw engagement with the threaded outer periphery 37 of the first receptacle 29. A slider 34 made of resin having a low friction coefficient, such as PTFE, is interposed between the first support plate 36 and the annular holder 38 which is fastened to the first receptacle 29.

The first friction plate 31 is made of resin. An engagement projection 303 protrudes from the lower surface of the plate 31 and fits in a first engagement hole 304 made in the first friction member 32. Hence, the first friction plate 31 is rotated together with the first friction member 32.

As shown in FIG. 17, the first friction member 32 has claws 305 protruding from the lower surface and extending parallel to the axis of the fixed shaft 18. The claws 305 are inserted in the engagement holes 306 made in the first support plate 36. Therefore, the first friction member 32 can rotate together with the first support plate 36. Connected to the first friction member 32, the first friction plate 31 can rotate along with the first support plate 36. When the annular holder 38 is threaded into the first receptacle 29, thereby pushing the first support plate 36 upwards. As a result, the bias applied from the first leaf spring 33 onto the first friction member 32 increases, and the pressure the first friction plate 31 applies onto the top wall of the annular chamber 30 (i.e., the lower surface of the first receptacle 29 increases eventually. Thus, it is possible to adjust the friction between the plate 31 and the lower surface of the first receptacle 29 to any desired value.

As shown in FIG. 4, a hollow cylindrical brake shaft 39 is located below the first support plate 36 and rotatably mounted on the first sleeve 22, with its upper end portion contacting the periphery of the first sleeve 22. A first mount plate 40 is located below slider 34 the first support plate 36 and fastened to the brake shaft 39 by a screw fastener 148. A second mount plate 41 is located below the first mount plate 40 and rotatably supported by the brake shaft 39. The screw fastener 148 is biased upwards by a screw 176, whereby the first mount plate 40 is firmly secured to the brake shaft 39.

As shown in FIG. 14, a projection 42 protrudes from the circumferential surface of the first mount plate 40. A stopper spring 43 and a bias spring 44 are fastened, at one end, to the first mount plate 40 by first fastening screws 174. The springs 44 and 45 are each a leaf spring. A rotation-restricting member 46 is mounted on the upper surface of the second mount plate 41 and fasted thereto by screws 47. The member 46 extends along the circumference of the first mount plate 40. It has an engagement recess 45 opening to the circumferential surface of the first mount plate 40. The projection 42 of the first mount plate 40 is located in the engagement recess 45. Therefore, the second mount plate 41 can rotate until the projection 46 abuts on either end of the engagement recess 45.

Two pins 48 extend through the second mount plate 41 and protrude upward from the upper surface of the plate 41. They are secured to the plate 41 at lower end by screws (not shown) and hold the other end portions of the springs 43 and 44 at upper end.

The first operation knob 49 is mounted on the first receptacle 29. The knob 49 has an upper surface and an outer circumferential surface which are smooth and continuous to each other, having no recesses in which dust and dirt may accumulate. The knob 49 has a projection 50 protruding from the inner circumferential surface into an engagement recess 51 made in the outer circumferential surface of the first receptacle 29. Hence, when the first operation knob 49 is rotated, the first receptacle 29 is rotated, and ultimately the first sleeve 22 is rotated.

A plurality of arcuate splines 309 are provided on the inner circumferential surface of the first operation knob 49. The splines 309 extend parallel to one another in the axial direction of the knob 49 and spaced apart from each other around the circumference of the knob 49 at predetermined pitch. A plurality of splines 310 are made in the outer circumferential surface of the annular holder 38 provided for adjusting the friction of the first friction plate 31. The splines 309 of the first operation knob 49 are fitted in the splines 310 of the annular holder 38. There would be no displacement between the annular holder 38 and the first operation knob 49. Nor would there be no disengagement between the threaded outer periphery 37 of the first receptacle 29 and the threaded inner periphery 37 of the annular holder 38. As a result, the friction between the top wall of the annular chamber 30 and the first friction plate 31 remains unchanged. Moreover, the annular holder 38 can be rotated to adjust the friction in unit of the pitch of the splines 309 and 310. The more splines and, hence, the shorter the pitch, the more minutely can the friction be adjusted.

As shown in FIG. 4, the first operation knob 49 has a first recess 52, which lightens the knob 49. A first lower cover 53 is fastened to the lower end of the knob 49, covering the first recess 52. The first lower cover 53 supports the brake mechanism 54 which is mounted on the upper end portion of the first sleeve 22, thus preventing the mechanism 54 from falling. The first sleeve 22, the first receptacle 29, the first operation knob 49 and the first lower cover 53 are fastened together, forming a unit.

Figure 19:
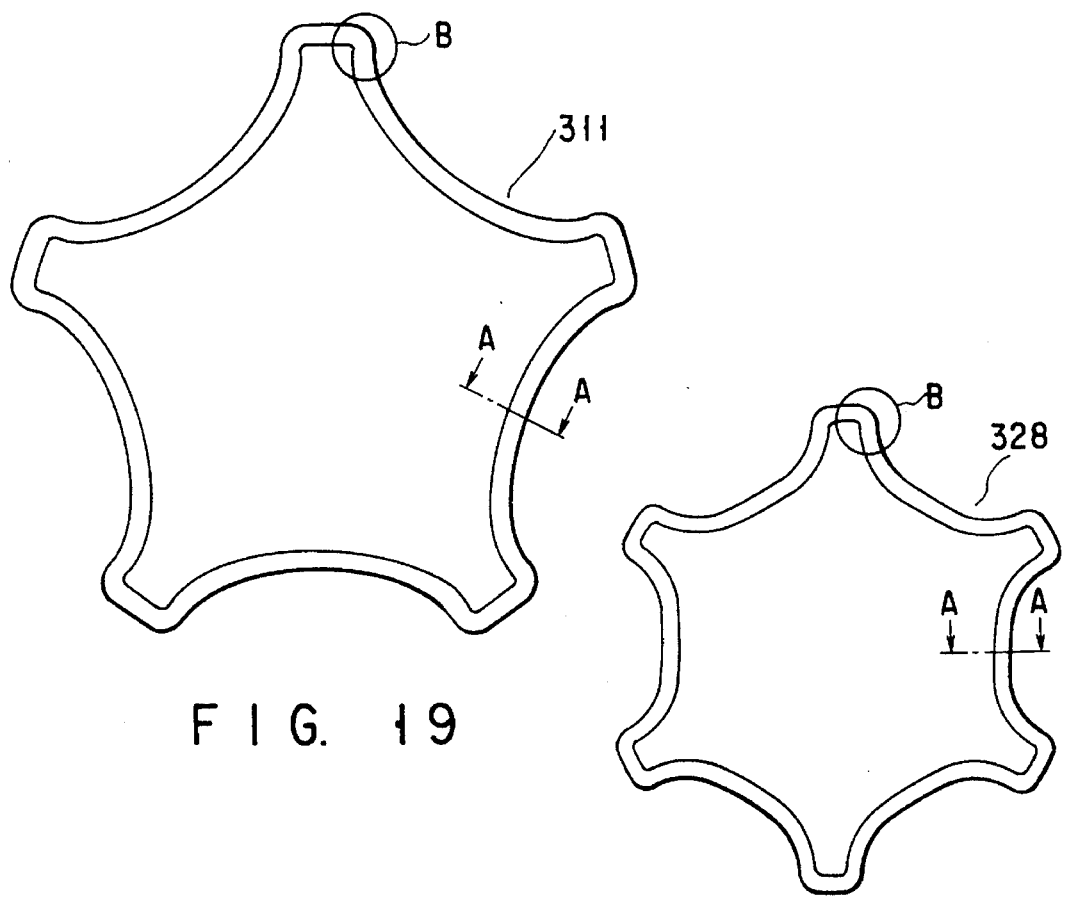
FIG. 19 is a plan view of the first seal member used in the first bending unit shown in FIG. 18.

The first lower cover 53 has a first seal groove 313 which is an annular groove. Fitted in the seal groove 313 is a first seal member 311. As shown in FIG. 19, the first seal member 311 is a pentagonal ring almost identical in outline to the first lower cover 53, and has a circular cross section of an O-ring. The first seal member 311 achieves watertight sealing between the first operation knob 49 and the first lower cover 53.

Figure 20:
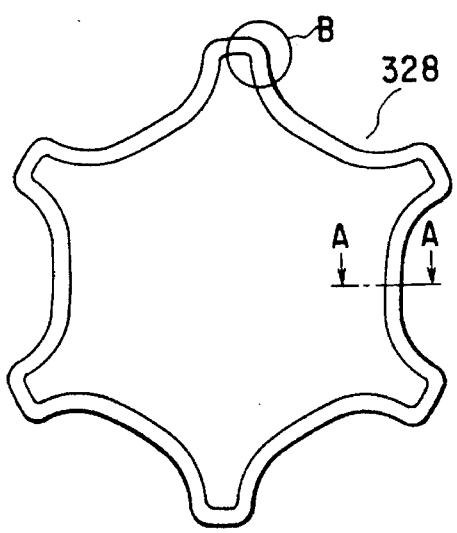
FIG. 20 is a plan view of the second seal member used in the first bending unit shown in FIG. 18.

As will be described later in detail, a second seal member 328 is interposed between the second operation knob 75 and a second lower cover 72. As shown in FIG. 20, the second seal member 328 is a hexagonal ring almost identical in outline to the second lower cover 72; it has a circular cross section of an O-rings. The second seal member 328 achieves watertight sealing between the second operation knob 75 and the second lower cover 72.

Figure 24:
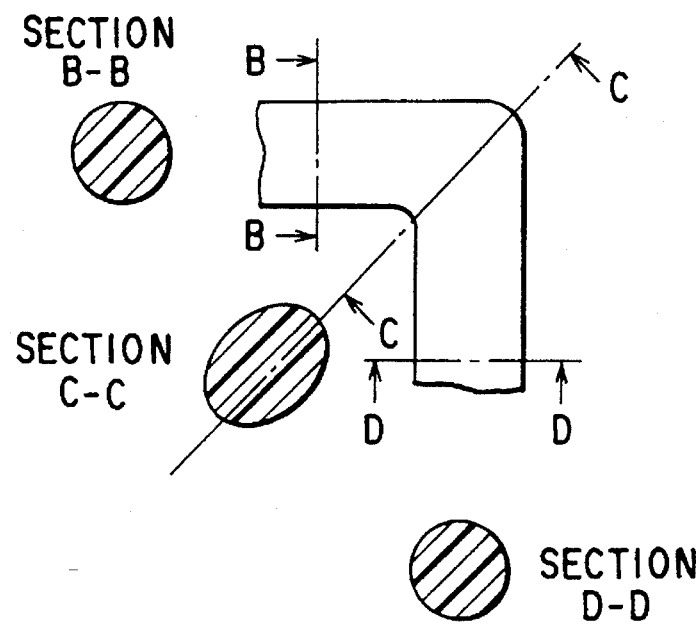
FIG. 24 is an enlarged view of the part B of either seal member shown in FIGS. 19 and 20.

The first seal member 311 has five bulging portions, whereas the second seal member 328 has six bulging portions. Each bulging portion of the first seal member 311 is aligned with the corresponding one of the bulging portions 355 (FIG. 14) of the first bending unit 20. Similarly, each bulging portion of the second seal member 328 is aligned with the corresponding one of the bulging portions 77 (FIG. 15) of the second bending unit 21. As shown in FIG. 24, either corner of any bulging portion of the seal members 311 and 328 has an elliptical cross section which is larger than the circular cross section of any other portion. This is because, for example, the first seal groove 313 in which the seal member 311 is placed is broader at each corner portion than at any other portion. Hence, the first seal member 311 provides watertight sealing between the first operation knob 49 and the first lower cover 53, whereas the second seal member 328 accomplishes watertight sealing between the second operation knob 75 and the second lower cover 72.

Figure 21:
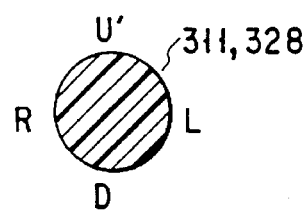
FIG. 21 is a sectional view taken along lines A—A in FIGS. 19 and 20.
Figures 22, 23:
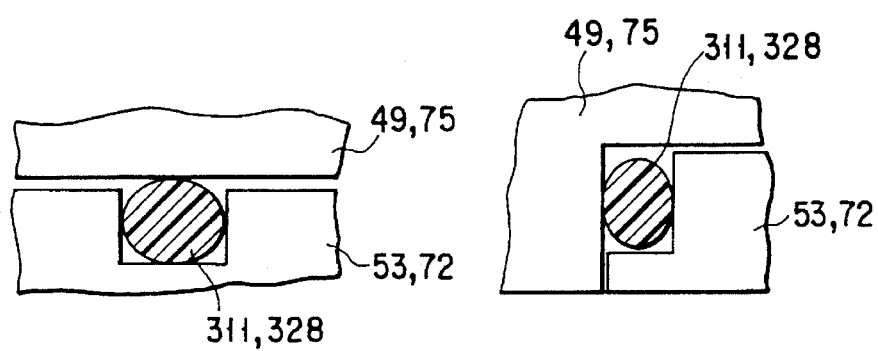
FIG. 22 is a sectional view illustrating how either seal member is clamped in the case where the operation knob is placed atop the lower cover.
FIG. 23 is a sectional view showing how either seal member is clamped in the case where the operation knob is positioned beside the lower cover.

FIG. 21 shows the cross section of either seal member, taken along line A—A in FIGS. 19 and 20. FIG. 22 illustrates how either seal member is clamped in the case where the operation knob is placed atop the lower cover. FIG. 23 shows how either seal member is clamped in the case where the operation knob is positioned beside the lower cover.

Having the specific shapes shown in FIGS. 19 and 20, the first seal member 311 and the second seal member 328 fit well in the seal grooves which are not circular. They can achieve watertight sealing required to miniaturize the components of the bending device and to enhance the operability of the bending device.

Seal members similar to the members 311 and 328 can be used to provide not only watertight sealing between an operation knob and a lower cover, but also watertight sealing between any two parts having different shapes. Needless to say, such a seal member may have a larger cross section at a portion other than a corner portion, than at any other portion.

As shown in FIGS. 4 and 14, the first lower cover 53 has projections 312 which protrudes parallel to the axis of the first operation knob 49 and arranged in a circle concentric to the knob 49. A stop plate 314 is arranged above the first seal groove 311. The plate 314 has holes 315, through which the projections 312 extend. The stop plate 314 prevents the first seal member 311 from slipping out of the first seal groove 311.

As can be seen from FIG. 14, the holes 315 have a diameter greater than the width of the projections 312. Claws 317 are held up from the longer edges of each hole 315. The claws 317 resiliently clamp the projection 312, whereby the stop plate 314 is secured to the first lower cover 53.

As has been described, the first operation knob 49 covers the not only the top but also the sides of the internal assembly comprising the first receptacle 29, the first friction plate 31, the first friction member 32, the first leaf spring 33, the slider 34, the first support plate 36, the annular holder 38 and the brake mechanism 54—which are arranged one upon another. The first recess 52 of the operation knob 49 has five recesses 318 shaped like a triangular ring and opening downwards. Fitted in these recesses 318 are the projections 319 which protrude upwards from the lower surface of the first cover 53. The recesses 318 are filled with adhesive, which hold the projections 319 firmly in the recesses 318. As a result of this, the first operation knob 49 and the first lower cover 53 are connected together.

As shown in FIG. 14, vents 357 are made in the first operation knob 49, each extending from one recess 318. As the recesses 318 are filled with the adhesive and as the projections 319 are inserted into the recesses 319, air is forced out through the vents 357. When the projections 318 are completely fitted in the recesses 319, no air remains in the recesses 319. If air remained in the recesses 319, it would inflate when the adhesive is heated to be dried, inevitably pushing the adhesive out of the recesses 319 and, thus, impairing the connection between the first operation knob 49 and the first lower cover 53. Since there is no air remaining in the recesses 319, the operation knob 49 and the first lower cover 53 are joined steadfastly.

It suffices to fill the adhesive in the recesses 319. In other words, the adhesive need not be coated on the inner surfaces of each recess 319. Therefore, much labor or time is not required to fasten the knob 49 and the cover 53 together. Since a mass of adhesive filled in each recess 319 is more conspicuous than a thin film of adhesive coated on any inner surface of the recess 319, it is easier than otherwise to locate the recess 319. This helps to facilitate the fastening of the cover 53 to the first operation knob 49. Furthermore, since each recess 318 is large, the adhesive does not overflow when the projection 318 is inserted into the recess 319.

As shown in FIG. 4, the second mount plate 41 has a notch 55. Set in the notch 55 is the projection 57 formed integral with the upper end of the brake plate 56. When the brake plate 56 is rotated in sliding contact with the brake shaft 39, the brake plate 57 and the second mount plate 41 will be rotated together. An O-ring 320 is interposed between the brake shaft 39 and the brake plate 56. The O-ring 320 applies a braking force on the brake plate 56 while the plate 56 is being rotated. The brake plate 56 has an annular groove in its circumferential surface. Fitted in the annular groove is an O-ring 58, which serves as a watertight seal between the brake plate 56 and the flange 59 formed integral with the first lower cover 53.

An operation lever 60 is fastened, at its inner end, to the brake plate 56 by a second fastening screw 175. When the lever 60 is rotated, the brake plate 56 is rotated, rotating the second mount plate 41. An operation knob 61 made of resin is adhered to the outer end of the operation lever 60. The intermediate portion of the lever 60 is covered by a heat-shrinking, electrically conductive tube 62. The knob 61 has height H (FIG. 3) and width B (FIG. 13) which are virtually equal to those of at least one of the bending units 20, 21 and 146. The first bending unit 20 has height h1 and width b1; the second bending unit 21 has height h2 and width b2; and the third bending unit 146 has height h3 and width b3.

As may be understood from the foregoing, the first sleeve 22, the first receptacle 29, the first operation knob 49 and the brake plate 56 constitute the first bending unit 20. The first bending unit 20 is fixed to the operation section 8 of the electronic endoscope 1 since the first sleeve 22 is mounted on the fixed shaft 18 and set in engagement with the first sprocket 24. The brake shaft 39, which is a hollow cylinder, is mounted on the bearing 27. The upper end portion 64 is a prism, and the hollow of the brake shaft 39 has a polygonal cross section. Thus, the bearing 27 and the brake shaft 39 cannot rotate relative to each other.

Figure 8:
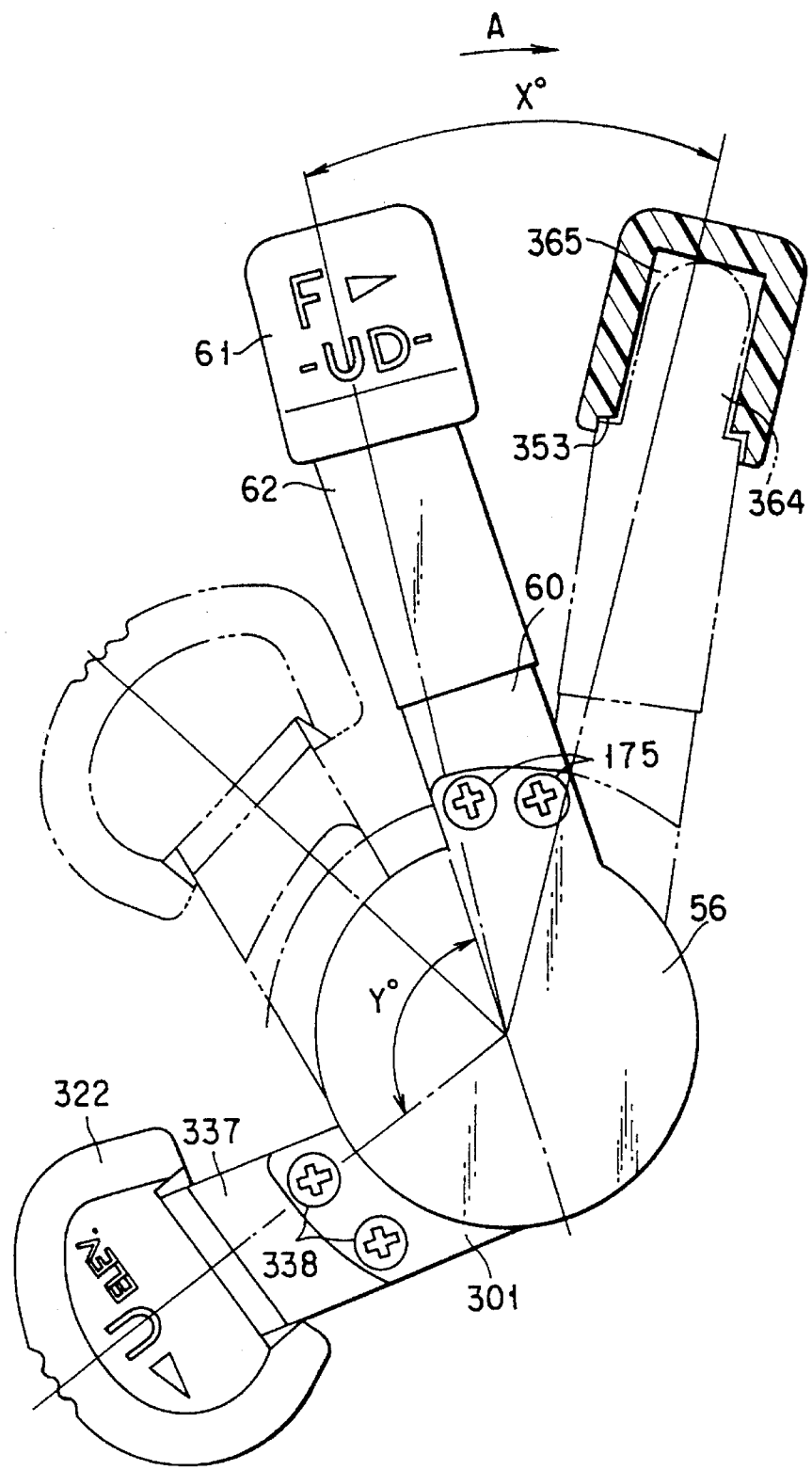
FIG. 8 is a plan view showing the positional relationship among the operation levers and the forceps-driving lever of the bending device.

When the operation lever 60 is rotated in the direction of arrow A through an angle of X°, as illustrated in FIG. 8, the pins 48 are moved, bending the stopper spring 43 and the bias spring 44 toward the axis of the first bending unit 20. When the free end of the stopper spring 43 abuts on one of the splines 35 provided on the inner periphery of the first support plate 36, the first support plate 36 is coupled to the first mount plate 40. The first support plate 36 is thereby stopped from rotating. In this case, it is the friction between the first receptacle 29 and the first friction plate 31 that does serve to rotate the first operation knob 49. In the case where the operation lever 60 is not rotated to actuate the brake mechanism 54, the first support plate 36 can be rotated together with the first friction plate 36 and the first friction member 32, as the operator rotates the first operation knob 49.

The angle of X°, by which the lever 60 is rotated, is not related with the angle of bending the flexible tube 10. Rather, the angle is constant. It follows that the operator need not be careful to rotate the operation lever 60 through the angle he or she thinks the best possible one. He or she only needs to rotate the lever 60 until the free end of the stopper spring 43 abuts on one of the splines 35. This also enhance the operability of the bending device which can bend the flexible tube 10 by any desired angle in any desired direction.

As the operator rotates the first operation knob 49 which is a component of the first bending unit 20, the rotation is transmitted from the flange 59 of the first lower cover 53 to the brake plate 56. Nonetheless, the O-ring 320 prevents the brake plate 56 from rotating. Namely, the brake mechanism 54 operates well, preserving the operability of the first bending unit 20. An O-ring may be used in addition to the O-ring 320, the O-ring 320 may be replaced with an O-ring having a larger cross section, or the O-ring 320 may be more depressed to increase the braking force, more reliably preventing the brake plate 56 from rotating.

The second bending unit 21 will described below, with reference to FIG. 5.

The second bending unit 21 has a second receptacle 65 which is mounted on the second sleeve 23. Mounted on the second receptacle 65 are a second leaf spring 66 and a second support plate 68. The leaf spring 66, which is a shaped annular spring, can move up and down. So can the support plate 58 which is located above the leaf spring 66. A second friction plate 67 is fixed on the second support plate 58. The receptacle 65, the leaf spring 66, the friction plate 67 and the support plate 58 are prevented from moving from the second sleeve 23, by the flange 69 which is formed integral with the upper end of the second sleeve 23. A disc 71 is mounted on the upper surface of the second friction plate 67. The disc 71 has a rectangular hole 70 in its center portion and can move up and down.

A second lower cover 72 is loosely mounted on the second sleeve 23 and located below the second receptacle 65. The second receptacle 65 is substantially rectangular, having a rounded four corners, and is fitted in the rectangular recess made in the upper surface of the second lower cover 72. Thus, the receptacle 65 cannot rotate relative to the cover 72. The second lower cover 72 clamped between the second receptacle 65 and a first fastener 73 set in screw engagement with the second sleeve 23. An O-ring 74 is interposed between the cover 72 and the fastener 73, providing watertight sealing between the cover 72 and the fastener 73. An O-ring 149 is interposed between the first fastener 73 and the first operation knob 49, achieving watertight sealing between the first fastener 73 and the first bending unit 20.

Figure 15:
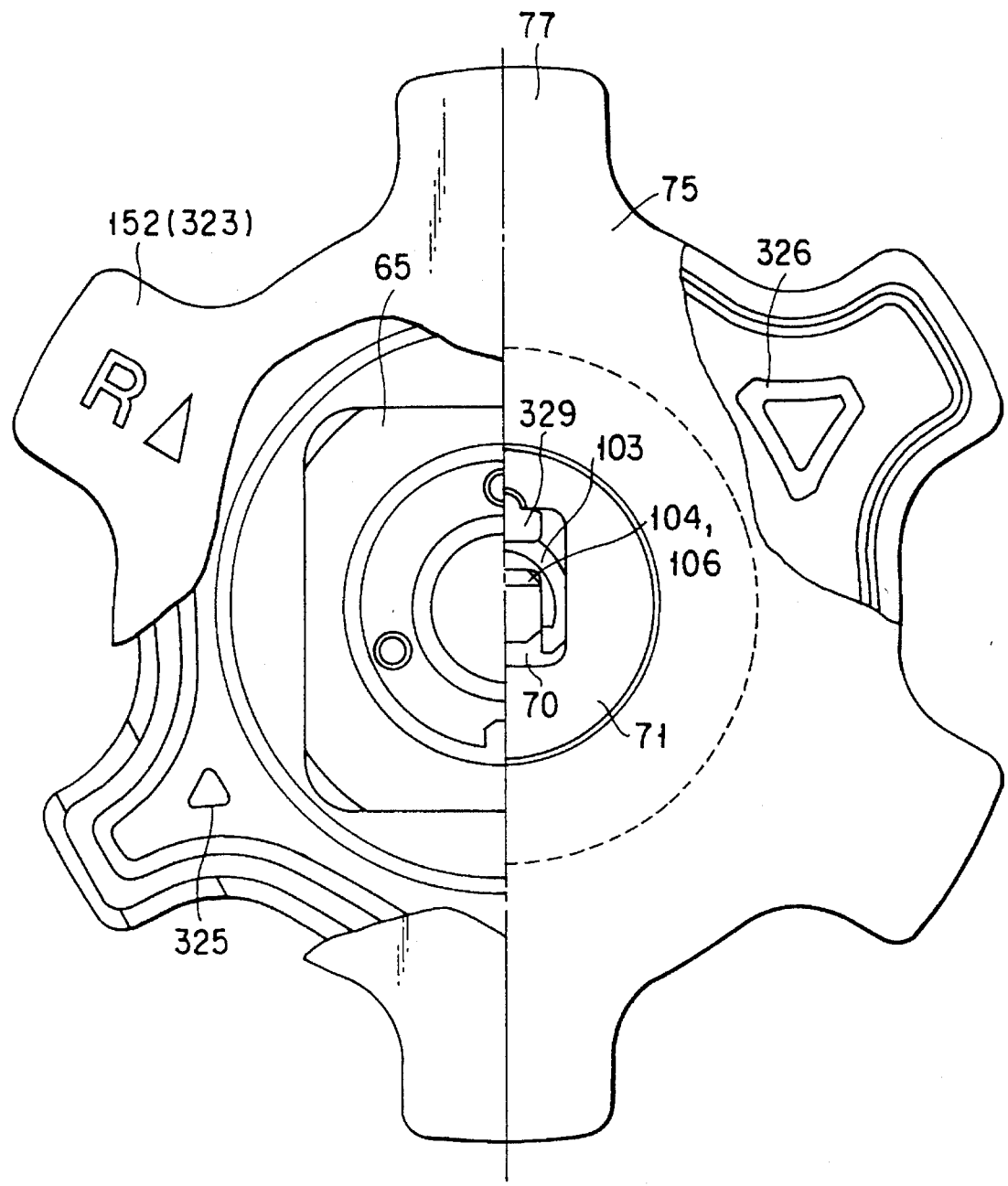
FIG. 15 is a partly sectional view showing the internal structure of the second bending unit of the bending device.

A second operation knob 75, which has an opening in its center portion, is located above the disc 71. The knob 75 has an upper surface and an outer circumferential surface which are smooth and continuous to each other, having no recesses in which dust and dirt may accumulate. The second operation knob 75 has a stepped portion 76 in its lower edge including bulging portions 77 (FIG. 15). The second lower cover 72 has its edge fitted in the stepped portion 76 of the second operation knob 75. Hence, there is displacement between the cover 72 and the knob 75 when the knob 75 is rotated in either direction.

As may be understood from the above, the second receptacle 65, the second leaf spring 66, the second friction plate 67, and the disc 71 are arranged above the second lower cover 72, one upon another in the order mentioned.

The second lower cover 72 has has six recesses 326, each shaped like a triangular ring and opening downwards. Fitted in these recesses 326 are the projections 325 which protrude upwards from the lower surface of the second operation knob 75. The recesses 326 are filled with adhesive, which hold the projections 325 firmly in the recesses 326. As a result of this, the second lower cover 72 and the second operation knob 75 are connected together. The cover 72 and the knob 75 are positioned with respect to each other since, as indicated above, the edge of the cover 72 is fitted in the stepped portion 76 of the second operation knob 75.

The second lower cover 72 has an annular seal groove 327 in its circumferential edge. Fitted in the seal groove 327 is the second seal member 328. As has already mentioned, the seal member 328 is a hexagonal ring almost identical in outline to the second lower cover 72 and has a circular cross section of an O-rings; it serves as a watertight seal between the second operation knob 75 and the second lower cover 72.

A plurality of columnar ribs 80 protrude upwards from the circumferential edge of the second lower cover 72. The ribs 80 prevent the disc 71 from moving in its radial direction and also prevent the adhesive overflowing the recesses 316 from flowing onto the disc 71 and some other components.

As described above, the second sleeve 23, the second receptacle 65, the disc 71 and the second lower cover 72 are fastened together, constituting the second bending unit 21.

The second bending unit 21 is mounted on the fixed shaft 18 after the first bending unit 20 has been mounted by mounting the second sleeve 23 on the shaft 18 and then set this sleeve 23 in engagement with the second sprocket 25. After the second bending unit 21 has been so mounted on the shaft 18, a stopper 103 is mounted on the shaft 18, preventing the unit 21 from slipping from the support shaft 18.

Figure 11:
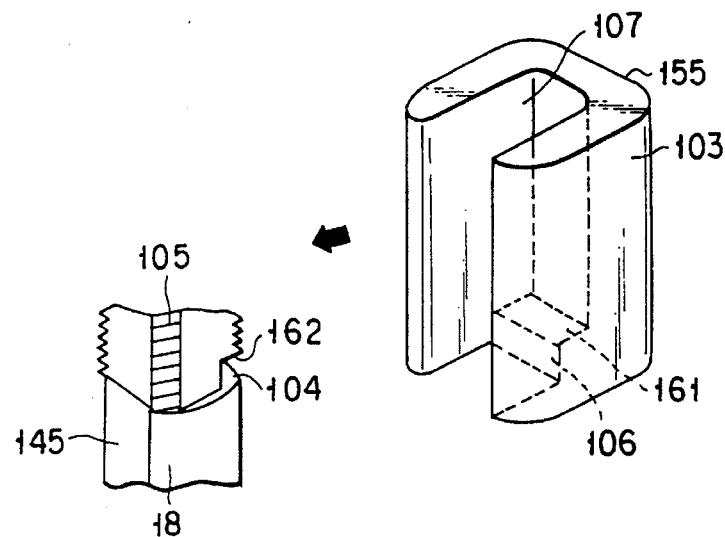
FIG. 11 is a perspective view explaining how the stopper is attached to the fixed shaft.

An O-ring 144 is interposed between the fixed shaft 18 and the inner periphery of the second sleeve 23, providing friction between the shaft 18 and the second sleeve 23. This friction restricts the rotation of the second bending unit 21 which occurs when the operator rotates the first bending unit 20 because of the O-ring 149 interposed between the first fastener 73 and the first operation knob 49. As shown in FIG. 11, an air passage 145 is defined between the fixed shaft 18 and the O-ring 144. The air passage 145 serves to determine whether the third bending unit 146 remains watertight or not, as will be explained later.

As shown in FIG. 11, the fixed shaft 18 has a notch 104 in that portion which is at the same level as the upper surface of the second bending unit 21. The upper end portion of the shaft 18, which extends upward from the notch 104, is a square prism. A brake-force adjusting screw 105 is cut in the four corners of the upper end portion of the shaft 18. Mounted on the upper end portion of the shaft 18 is the stopper 103.

As shown in FIG. 11, the stopper 103 is a square prism having rounded four corners and a U-groove 107. It is thus a trough-shaped member. The four sides of the stopper 103 have almost the same length, which is slightly less than the either short side of the rectangular hole 70 made in the disc 71. The U-groove 107 is slightly broader than each side of the upper end portion of the shaft 18. The stopper 103 is fitted, in part, in the notch 104 of the fixed shaft 18. It can be disengaged from the notch 104 when moved from the shaft 18 along the long sides of the rectangular hole 70 of the disc 71.

Figure 12:
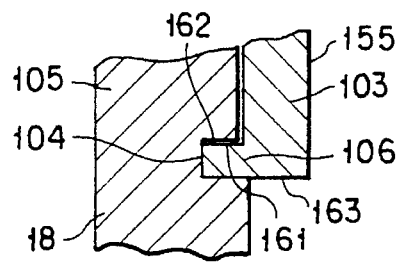
FIG. 12 is an enlarged sectional view of the fixed shaft and the stopper, explaining how the stopper is set in engagement with the fixed shaft.

The stopper 103 has a stepped portion 106 in the lower end of the groove 107. As illustrated in FIG. 12, the stepped portion 106 is fitted in the notch 104. Once the stepped portion 106 has been fitted in the notch 104, its top 161 abuts on the upper edge 162 of the notch 104. Hence, the stopper 103 can no longer be moved upwards or downwards unless it is moved away from the shaft 18 along the long sides of the rectangular hole 70 of the disc 71. Thus does the stopper 103 prevents the second bending unit 21 from disconnected from the first bending unit 20. Also does the stopper 103 prevents the disc 71 from rotating around the fixed shaft 18.

Figure 10:
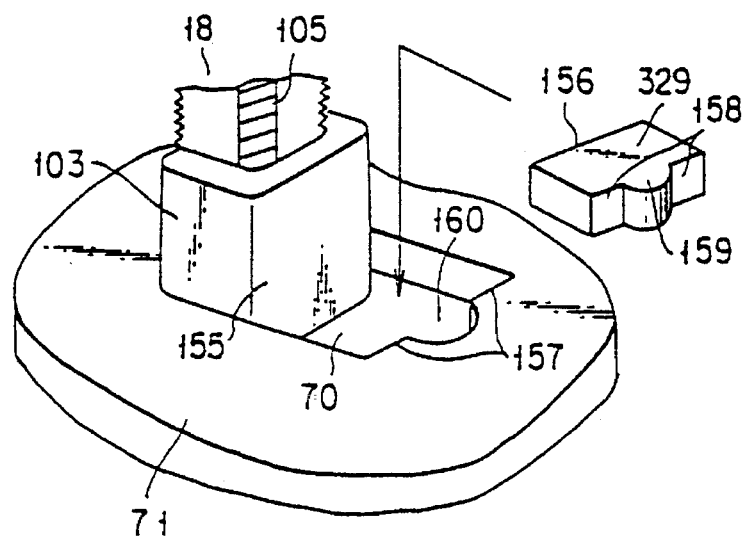
FIG. 10 is a perspective view explaining how a stopper, a disc and a fastener are secured to the fixed shaft of the bending device.

As shown in FIG. 10, a member 329 is fitted in the rectangular hole 70, more precisely in the gap between the stopper 103 and one edge 157 of the hole 70, thereby preventing the stopper 103 is prevented from moving away from the fixed shaft 18. The member 329 is a rectangular plate having two longer sides 156 and 158. The first side 156 abuts on the short side 155 of the stopper 103. The second side 158 has a semicircular projection 159 which is fitted in a U-notch 160 cut in said edge 157 of the hole 70. The projection 159 can be held with fingers, which facilitates the fitting of the member 329 into the gap between the stopper 103 and one edge 157 of the hole 70.

The member 329 is prevented from lifting by the lower end of a pusher member 108. As shown in FIG. 5, the pusher member 108 is comprised of a second fastener 110 and a third mount plate 111. Therefore, the member 103 is firmly secured to the fixed shaft 18.

The pusher member 108 pushes the disc 71 is pushed onto the second friction plate 67. The friction between the second friction plate 67 and the disc 71 can be adjusted by rotating the second fastener 110 and the third mount plate 111. The second fastener 110 supports a third lower cover 109, is set in screw engagement with the third mount plate 111, and has its upper end abutting on the upper end of the third mount plate 111. Hence, the pusher member 108 can freely rotate in the space between the fixed shaft 18 and the third lower cover 109.

Figure 5:
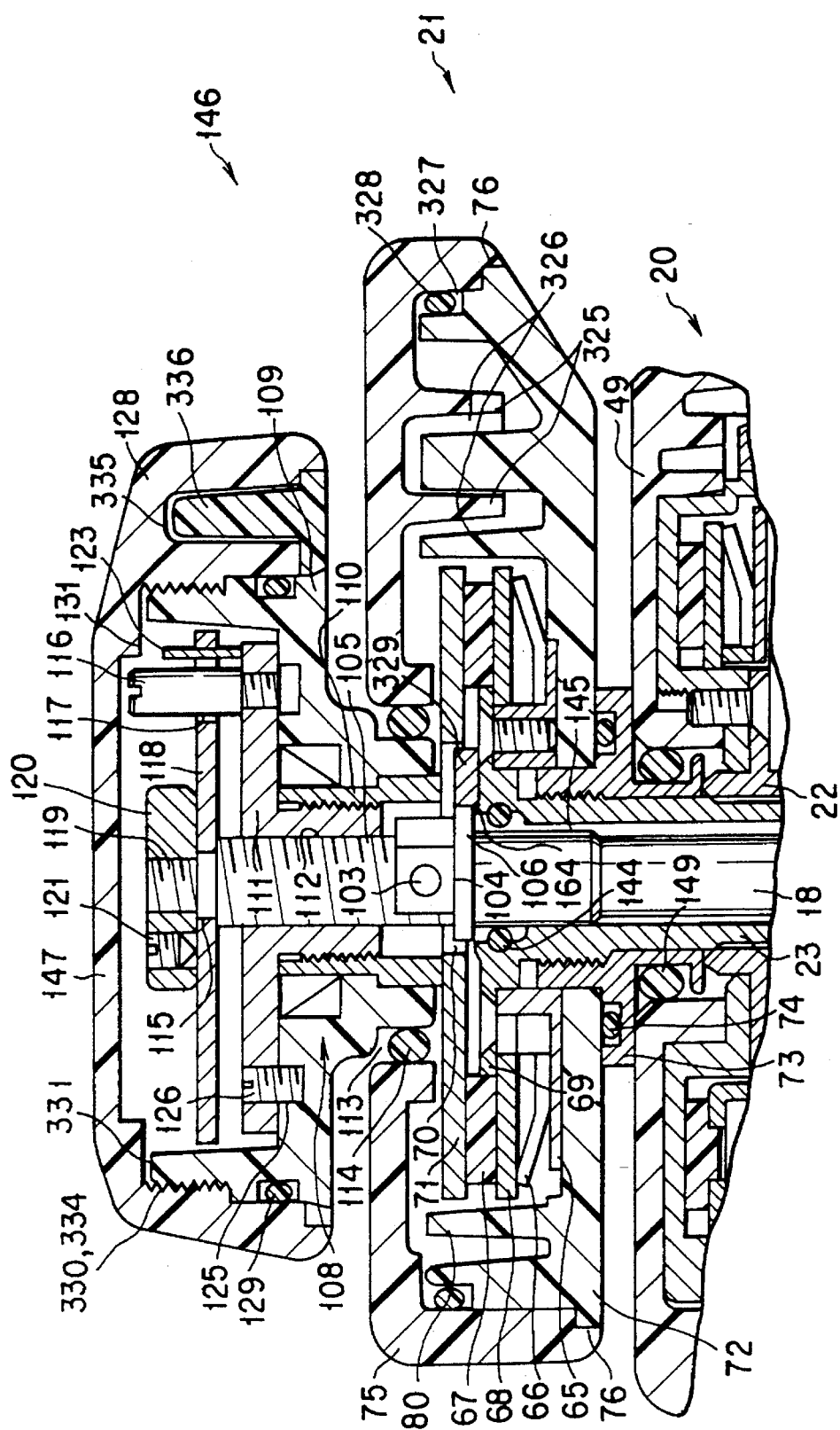
FIG. 5 is a side sectional view of the second and third bending units of the bending device shown in FIG. 3.

As seen from FIG. 5, the lower end portion of the second fastener 110 protrude from the lower surface of the third cover 109. Thus, it is the lower end of the second fastener 110 that pushes the disc 71. The third mount plate 111 has a female screw 112 which is placed in engagement with the brake-force adjusting screw 105 cut in the upper end portion of the shaft 18. The third mount plate 111 is thereby connected to the fixed shaft 18. An O-ring 114 is mounted on the lower end of the third lower cover 109, securing watertight sealing between the second operation knob 75 and the third lower cover 109.

As is shown in FIG. 16, the upper end portion of the fixed shaft 18 includes a square prism 115 which is thinner than that portion in which the brake-force adjusting screw 105 cut and which is eccentric to the fixed shaft 18. Mounted on the square prism 115 is a rotation-restricting plate 118. The plate 118 is fastened by screws to the third mount plate 111 and has a groove 117 and a square hole 118a. The prism 115 is fitted in the square hole 118a of the plate 118 which is secured to the third mount plate 111. As a result, the prism 115 cannot rotate relative to the rotation-restricting plate 118 and is oriented with respect thereto. A screw 119 is cut in the upper portion of the prism 115. A third fastener 120 is mounted in screw engagement with the screw 119 and thus fastened to the rotation-restricting plate 118. The third fastener 120 is biased upwards by a set screw 121 and connected to the screw 119 steadfastly.

The resistance to rotation which the second bending unit 21 has is the friction between the second friction plate 67 and the disc 71 which is biased onto the plate 67 by the pusher member 108 set in screw engagement with the fixed shaft 18. This resistance is adjusted by rotating the pusher member 108, whose rotation is restricted by the rotation-restricting plate 118. It follows that the resistance is adjusted in unit of the angle which the plate 118 sets and through which the pusher member 108 can rotate.

As shown in FIG. 16, a plurality of the screw holes 122 are formed in the third mount plate 111 and spaced apart along the circumference of the plate 111. In assembling the second bending unit 21, the pusher member 108 is rotated in screw engagement with the fixed shaft 18, thereby providing a desired rotation-resistance. Then, a stop pin 116 is inserted into the hole made in the plate 118 and located at an edge of the groove 117 and further into that one of the screw holes 122 which happens to be right below the hole of the rotation-restricting plate 118. Hence, the rotation-resistance of the second bending unit 21 can be adjusted various values as many as the screw holes 122 of the third mount plate 111. In this embodiment, the plate 111 has eighteen screw holes 122, and the resistance can be adjusted to eighteen values. Needless to say, the more screw holes 122, the more minutely can the rotation-resistance be adjusted.

In the present embodiment, the brake-force adjusting screw 105 is a left-handed one. Thus, the rotation-resistance of the second bending unit 21 will become maximum if the stop pin 116 is fixed at the left edge of the groove 117; it will become minimum if the stop pin 116 is fixed at the right edge of the groove 117. A click spring 123 is mounted on the upper surface of the third mount plate 111. The click spring 123 has its free end resiliently abutting on the stop pin 116 while the pusher member 108 is rotating through an angle defined by the groove 117.

The third lower cover 109 is fastened to the pusher member 108 by a set screw 126 placed in one of the screw holes 122 of the third mount plate 111. The cover 109 therefore rotates together with the pusher member 108. As shown in FIG. 16, alphanumeric letters 332 are put on the upper surface of the third lower cover 109, spaced apart along the circumference of the cover 109. To fasten the cover 109 to the pusher member 108 at a predetermined position with respect thereto, the cover 109 is rotated until the letter 332 indicating the predetermined position reaches the pointer 333 connected to the rotation-restricting plate 118. Next, the set screw 126 is driven through the one of the screw holes 122 into the hole 125 which is made in the third lower cover 109 and which is aligned with the hole 122. The third lower cover 109 can no longer rotate relative to the third mount plate 111 and is fixed at the predetermined position.

As shown in FIG. 16, bulging portions 124 protrude from the circumferential surface of the third lower cover 109. The bulging portions 124 improve the operability of the third bending unit 146, the bulging portions 355 (FIG. 14) and the bulging portions 77 (FIG. 15) enhance that of the first bending unit 20 and that of the second bending unit 21. The third operation knob 128 has bulging portions 124, too.

As shown in FIG. 5, a third operation knob 128 is fastened to the third lower cover 109 since the female screw 330 cut in the inner periphery of the knob 128 are set in mesh with the male screw 334 cut in the outer periphery of the third lower cover 109. Adhesive is applied in the gap between the screw 330 and the screw 334, whereby the knob 128 and the cover 109 are firmly joined together. The third operation knob 128 has an upper surface and an outer circumferential surface which are smooth and continuous to each other, having no recesses in which dust and dirt may accumulate. An O-ring 129 is fitted in an annular groove cut in the outer circumferential surface of the third lower cover 109. This O-ring 129 makes a watertight seal between the cover 109 and the third operation knob 128.

Both the third lower cover 109 and the third operation knob 128 are resin moldings. Hence, once they have been fastened together, with the screws 330 and 334 set in mesh, their relative positions remain unchanged at all. Were their relative positions to change, they should be made by using different molds. Only if the cover 109 is rotated until the letter 332 indicating the prescribed position reaches the pointer 333 and then the third lower cover 109 and the third operation knob 128 are joined together, the bulging portions 124 of the cover 109 are aligned with the bulging portions 124 of the knob 128. This ensures the operability of the third bending unit 146. The click spring 123 is prevented from falling by a spring holder 131 which is formed integral with the third operation knob 128.

The bending device 13 can be overhauled by removing its components in the order reverse to the order they have been assembled together. Thus, the third operation knob 128, the set screw 121 and the third fastener 120, for example, are removed in the order they are mentioned.

The third operation knob 128 is firmly fastened as described above, and it seems likely that much time and labor would be required to remove the knob 128. On the contrary, the knob 128 can be easily removed since its the top wall 147 of the knob 128 is thinner than the side walls and can be cut easily. Once the top wall 147 of the knob 128 have been cut away, exposing the set screw 121 and the third fastener 120, the set screw 121 can be unscrewed and the third fastener 120 can be disengaged from the fixed shaft 18. Ultimately, the third operation knob 128 can be removed.

Nonetheless, the top wall 147 of the knob 128 is not broken by accident. For example, when the bending device 13 falls onto the floor and the knob 128 hit the floor. The top wall 148 may elastically bent and contact the third fastener 120 before it is broken. As a result, the impact the top wall 148 has received is absorbed by the fastener 120 which is thick and rigid and secured to the shaft 18 steadfastly.

As can be seen from FIG. 5, the four bulging portions 124 of the third operation knob 128 are made comparatively thick. A deep recess 335 is made in the lower surface of each bulging portion 124, facilitating the resin-molding of the knob 128. The recess 335 is filled with a projection 336 and adhesive. The lower surface of the third bending unit 146 is thereby rendered flat and smooth and can be washed more easily than otherwise. Four projection 336 filling the recesses 335 of the bulging portion 124 may be replaced by a one-piece member having four projections.

The angle of X°, by which the knob 128 of the third bending unit 146 is rotated, does not depend on the angle of bending the flexible tube 10. Rather, the angle is constant. Therefore, the operator need not be careful to rotate the knob 128 by the angle which he or she thinks the best possible one. The operability of the bending device 13 is thus increased, making it very easy for the operator to bend the flexible tube 10 by any desired angle in any desired direction.

The forceps-driving unit 324 will be described in further detail, with reference to FIGS. 6 and 7.

As described above, the bearing 27 has one end fastened to the cover 26 covering the base plate 17 and is located in the hole 19 of the housing 16, and the ring 301 is rotatably mounted on the bearing 27 and supported by a support shaft 28. As already indicated, the first O-ring 139 and fourth O-ring 360 are mounted on the support shaft 28, providing a watertight seal between the housing 16 and the shaft 28 and a watertight seal between the shaft 28 and the ring 301. As described above, the second O-ring 140 and the third O-ring 302 are mounted on the bearing 27, respectively forming a watertight seal between the bearing 27 and a brake plate 56 and a watertight seal between seal between the bearing 27 and the ring 301.

Figure 6:
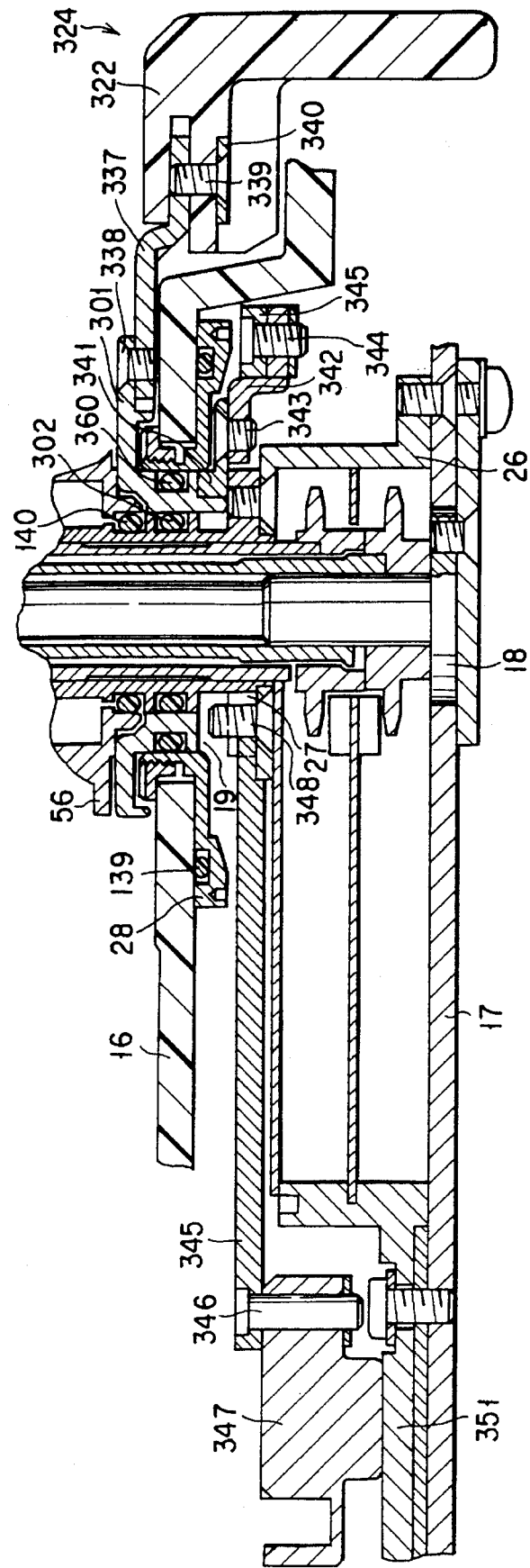
FIG. 6 is a side sectional view the forceps-driving unit incorporated in the bending device of FIG. 3.
Figure 7:
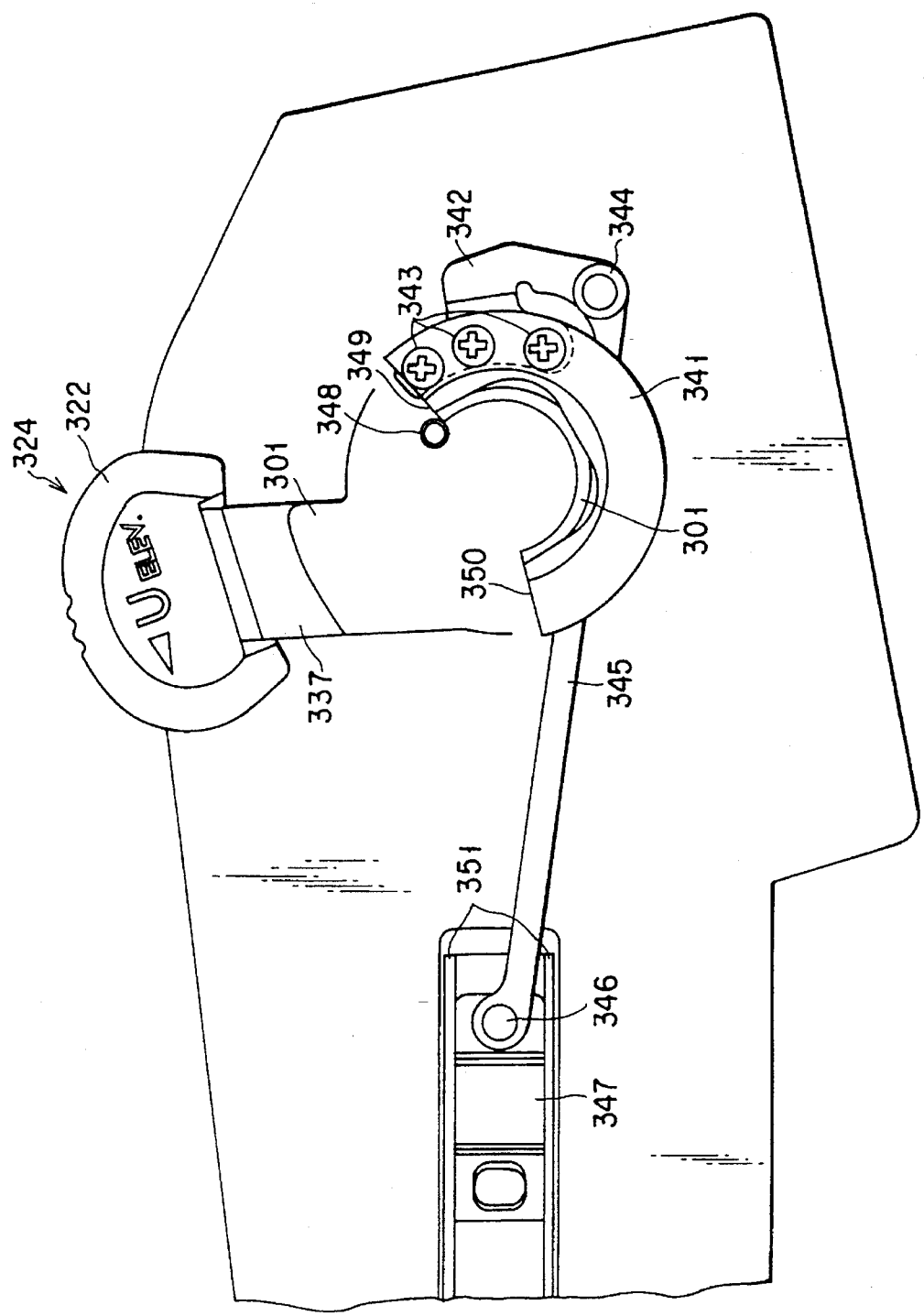
FIG. 7 is a plan view showing the forceps driving unit.

As shown in FIG. 6, a forceps-driving lever 337 is fastened at one end to the ring 301 by a screw 338. A knob 322 made of resin is connected to the other end of the forceps-driving lever 338. The knob 322 is clamped between the lever 337 and the plate 340 which are fastened together by a screw 339. The lower end of the ring 301 is a square prism having rounded corners and is fitted in a square hole made in a bearing 341 which is rotatable inserted in the support shaft 28. Thus, the ring 301 is rotated along with the bearing 341. A first link 342 is connected, at one end, to the lower end of the bearing 341 by a first link-fastening screw 343. A second link 345 is rotatably connected, at one end, to the other end of the first link 342 by a first pin 344. The other end of the second link 345 is rotatably connected a base 347 by a second second pint 346. As shown in FIG. 7, the base 347 is interposed between two guide walls 351 having a U-shaped cross section.

The rotation of the ring 310 can therefore be transformed to linear motion of the base 347 by means of the bearing 341 and the first link 342. As the base 347 moves back and forth, it pulls and slackens the operation wire connected to a forceps holder (not shown) rotatably connected to the distal end of the rigid tube of the insertion section 9. The forceps holder is thereby rotated at a desired angle, and the forceps held by the holder is held up.

The ring 301, the bearing 341 and the first link 342 have a sector-shaped notch each. The bearing 341 has two surfaces 349 and 350 which abut on a stopper screw 348 which is one of the screws fastening the cover 26 and the bearing 27 together, which is longer than any other screws. The ring 301 and the bearing 341 can rotate, but over the distance between the surfaces 349 and 350 of the bearing 341. The motion of the second link 345 and the base 347 are thereby limited, and so is the angle by which the forceps holder can be held up.

The stopper screw 348 and the surface 349 are so positioned that the knob 322 assumes the same position in the forceps-driving unit 324 or is inclined at the same angle (angle of Y°), when the base 347 is held up at whatever maximum angle. Thus, the operator can determine from the position of the knob 322 whether or not the base 347 is held up at the maximum angle. An excessive turning of the knob 322 can therefore be prevented. This also improve the operability of the bending device 13.

The brake mechanism 54 of the first bending unit 20 and the forceps-driving unit 324 are located, one above the other, on the housing 16 of the operation section 8, and the brake plate 56 and the ring 301 have the same outer diameter. Hence, the bending device 13 has no recesses in its outer surface, in which dirt and dust may accumulate. The outer surface of the device 13 can be washed well with a brush and can be dried fast. Furthermore, since the operation lever 60 and the forceps-driving lever 337 are located at the same height, they can be operated by the same hand. They can be rotated but only in the opposite directions, and do not interfere with each other when operated at the same time.

As shown in FIG. 8, the operation lever 60 and the forceps-driving lever 337 are extend from the brake plate 56 in parallel to each other, not in the radial direction of the plate 56. This also serves to prevent the interference between the levers 60 and 337. In addition, since the operation knob 61 and the knob 322 extend in the radial direction of the brake plate 56, the knobs 61 and 332 appear as if moving in concentric circles, though they are actually moved in eccentric circles. This enhances the operability of the bending device 13, as well.

As shown in FIG. 8, the operation lever 60 has an end portion 364 which is less broader than the other portion. The end portion 364 of the lever 60 is inserted in the hole 365 made in the operation knob 61, and the gap between the end portion 364 and the inner surface of the hole 365 is filled with adhesive. The knob 61 is thereby connected to the operation lever 60. The heat-shrinking tube 62 covering the lever 60 is also inserted in the hole 365 of the knob 61 and fitted therein, too. The operation knob 61 is thus connected to the operation lever 60, without making the knob 61 broader than the operation lever 60. Relatively small, the operation knob 61 is easier to hold with fingers and less likely to be touched by mistake.

Figure 9:
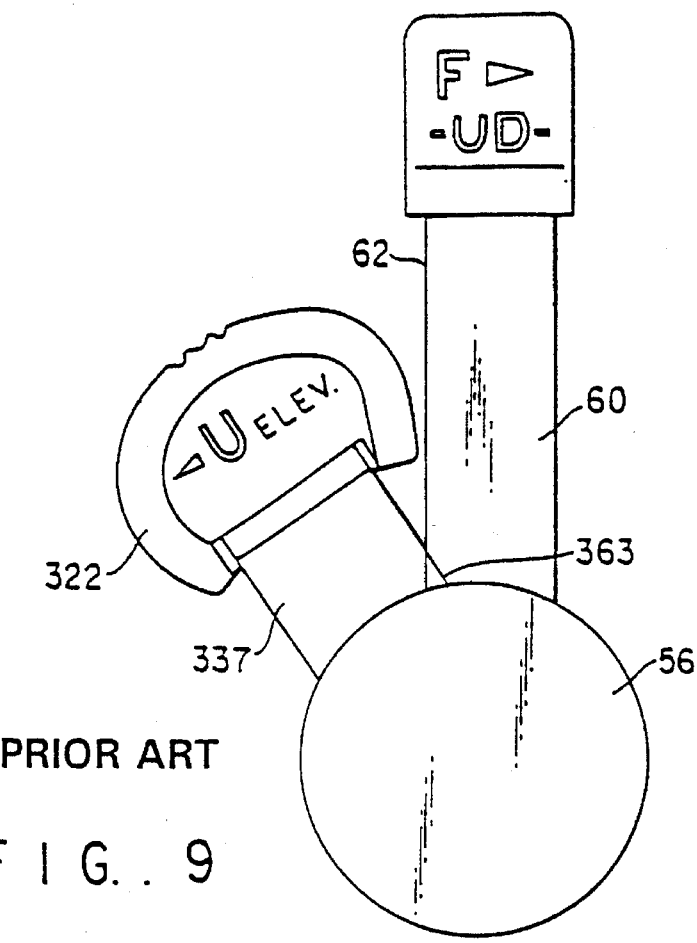
FIG. 9 is a plan view illustrating the positional relationship between the operation lever and the forceps-driving lever of a conventional bending device.

FIG. 9 illustrates the arrangement of a forceps driving lever 337 and a brake operation lever 60 of a conventional bending device. In most conventional bending devices, the levers 60 and 337 are located at different levels so that they may not interfere with each other. In some conventional bending devices, the levers 60 and 337 are located at the same level to improve the operability of the device, but cannot be rotated through so large an angle that they may interfere at portions 363 (FIG. 9), and the forceps holder cannot be held up by large angles. With any bending device wherein the levers 60 and 337 are placed at the same level, the levers 60 and 337 must be rotated through a small angle and in the clockwise direction and the counterclockwise direction, respectively.

In the bending device 13 according to the present invention, the brake plate 56 and the ring 301 are located one above the other as is illustrated in FIG. 8. Moreover, the operation lever 60 and the forceps-driving lever 337 are rotated around different points. Hence, the levers 60 and 337 can located at the same level and can be rotated through a relatively large angle.

Figure 13:
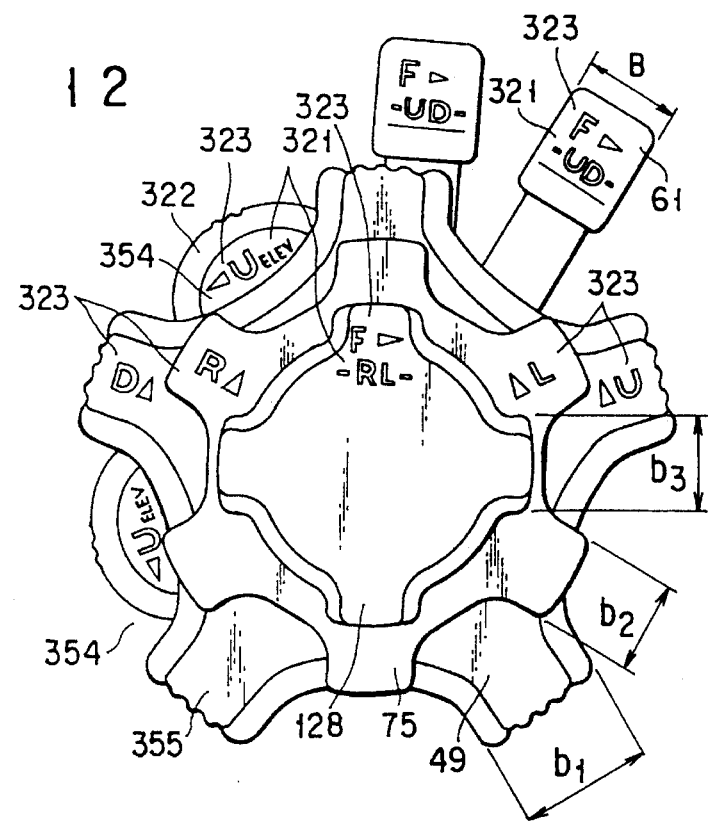
FIG. 13 is a plan view of the bending device.

As seen from FIG. 13, signs 152 are put on the upper surfaces of the knobs 49, 75, 128, 61 and 322, indicating the operations which the knobs are to perform and the directions in which they are to be rotated or moved. To be more specific, the first operation knob 49 has a sign "UD" for "UP/DOWN," meaning that the flexible tube 10 will be bent up or down when the first bending unit 20 is operated. The second operation knob 75 has a sign "RL" for "RIGHT/LEFT," indicating that the tube 10 will be bent to the right or the left when the second bending unit 21 is operated. The operation knob 61 has two signs "F" and "UD." The sign "F" indicates that a rotation resistance will be released from the first bending unit 20 when the knob 61 is pushed in the direction of the arrow "z,900 ," whereas the sign "UD" means that a rotation resistance will be added to the unit 20 when the knob 61 is moved up or down. The third operation knob 128 has two signs "F" and "RL." The signal "F"

indicates that a rotation resistance will be released from the second bending unit 21 when the third oppression knob 128 is pushed in the direction of the arrow "z,900," whereas the sign "RL" means that a rotation resistance will be added to the unit 21 when the knob 128 is moved to the right or the left. The knob 322 has two signs "U" and "ELEV." The signs "U" and "ELEV." mean that the forceps holder will be held up when the knob 322 is rotated in the direction of the arrow.

The sign "F" and "U" represent main functions, whereas the signs "UD" and "RL" indicate sub-functions. The signs "F" and "U" are located outer and larger than the signs "UD" and "RL" so that they may be more conspicuous. Similar signs may be put on some components of the endoscope system (e.g., the suction control section, the air/water supply section, the forceps insertion section and the control switches), each designed to perform a main function and a sub-function. The signs "F," "U," "UD" and "RL" are put in horizontal planes so that all of them may be fully seen when the bending device 13 is seen from the above.

As can be understood from FIG. 13, the operation knob 61 has a larger outer diameter than the first bending unit 20, the second bending unit 21 and the third bending unit 146. The first bending unit 20 has the second largest outer diameter, the second bending unit 21 the third largest diameter, and the third bending unit 146 the smallest outer diameter. Further, at least while remaining in the held-up position, the knob 322 is located at a finger rest 354 which is the gap between adjacent two of the five bulging portions 355 of the first bending unit 20. Therefore, the signs put on all knobs 49, 75, 128, 61 and 322 can be seen when the bending units 20, 21 and 146 and the forceps-driving unit 324 are located at their initial positions. Thus, the operator can understand, at a glance of the bending device 13, the functions of the units 20, 21, 146 and 324. The maximum angle at which the forceps holder (not shown) can be held up may be of such a value that the knob 322 may be located at the finger rest 354.

In the conventional bending device (FIG. 9), each of the letters and arrows forming the signs consists of a groove filled with color coating material. When dried, the coating material shrink, forming a recess. Dust and dirt is likely to accumulate in this recess. In the device 13 of the present invention, each letter and arrow of the signs 152 on the knobs 49, 75, 128, 61 and 322 consists of two slender grooves filled with color coating material. The recesses, which the color coating material forms when it shrink as it is dried, are so narrow and shallow that far less dust or dirt accumulates, if any, in them. Alternatively, the signs 152 may be printed ones or may be defined by tiny pits formed in the upper surfaces of the knobs 49, 75, 128, 61 and 322.

Of the bending sections 20, 21 and 146, the first bending unit 20 receives the greatest force since it is entirely held in the operator's hand. The fingers rest not only on the finger rest 354, but also on all five bulging portions 355. To prevent fingers from slipping on the bulging portions 355, the bulging portions 355 have serrations 359 in their outer surface as is shown in FIG. 14.

As described above, the first bending unit 20 is rotated to bend the flexible tube 10 up or down, the second bending unit 21 is rotated to bend the tube 10 to the left or the right, and the third bending unit 146 is rotated to control the rotation of the second bending unit 21. The operation lever 60 projecting from the braking plate 56 is rotated to control the rotation of the first bending unit 20, and the forceps-driving unit 324 is rotated to adjust the angle at which to hold up the forceps holder. In addition, the housing 16 and the bending units 20, 21 and 146 are watertight, and watertight sealing is achieved between the bearing 27 and the brake plate 56 and also between the bearing 27 and the ring 301. Thus, the operation section 8 of the electronic endoscope 1 remains watertight at all times.

Moreover, the first operation knob 49 and the first lower cover 53 constitute a housing which contains all other parts of the first bending unit 20 and all outer surfaces of which are smooth and continuous. Similarly, the second operation knob 75 and the second lower cover 72 form a housing which contains all other parts of the second bending unit 21 and all outer surfaces of which are smooth and continuous, and the third operation knob 128 and the third lower cover 109 form a housing which contains all other parts of the second bending unit 21 and all outer surfaces of which are smooth and continuous. This means that the bending device 13 hardly gets dirty and can easily be cleaned by washing. It is desirable that the knobs 49, 75 and 128 be made of electrically insulating material.

In the embodiment described above, the abutting surface of the first fastener 73 is located in the gap between the first bending unit 20 and the second bending unit 21, and the O-ring 114 is interposed between the second bending unit 21 and the third bending unit 146. The first fastener 73 and the O-ring 114 therefore define stepped portions. Since these stepped portions are located near the axis of the bending device 13, they are not touched by the operator at all and are most unlikely to get dirty. Thus, the bending device 13 has neither stepped portions nor recesses in which dust or dirt may accumulate, and is therefore easy to keep clean.

The upper surface and the circumferential surface of any bending unit of the device 13 have no grooves or no recesses, except the serrations 359 formed in the outer surface of each bulging portion 355 of the first operation knob 49. This also makes the bending device 13 easy to keep clean.

As can be seen from FIG. 3, the upper surfaces of the first operation knob 49 and the third operation knob 128 incline downwards toward the circumferences. Therefore, on the upper surfaces of these knobs 49 an 128, liquid such as cleaning water can easily flow from the center to the circumference. Furthermore, the lower surface of the second bending unit 21, which opposes the upper surface of the first operation knob 49, inclines upwards at the circumferential portion. The gap between the first bending unit 20 and the second bending unit 21 flares toward outside. A bush or any other washing tool therefore has easy access to that gap, which facilitates the cleaning of the bending units 20 and 21. Since watertight sealing is provided between the first lower cover 53 and the first operation knob 49, between the second lower cover 72 and the second operation knob 75, and between the third lower cover 109 and the third operation knob 128, the cleaning water would not flow into the operation section 8 of the electronic endoscope 1. In addition, the bending device 13 has no parts which are hardly accessible for a brush, it can be washed with ease.

The uppermost operation knob of the operation section of a conventional endoscope, which is equivalent to the third operation knob 128, has a projection extending upwards from the center part. This projection is provided so that an operator may easily rotate the operation knob by one hand, while holding the operation section in the other hand. The projection, however, renders the operation section lengthy and difficult to handle. Further, the projection may be broken if the operator drops the operation section onto the floor or bumps it against wall. By contrast, having a flat upper surface, the third operation knob 128 neither makes the operation section 8 lengthy nor is likely to be broken.

In the conventional bending device, an O-ring is interposed between the operation knob and the lower cover, and adhesive is applied on the abutting surfaces of the knob and the cover, fastening the knob and the cover together. It remains unknown which achieves the watertight sealing between the knob and the cover, the O-ring or the adhesive. Even if the O-ring fails to perform its function, this cannot be detected before the adhesive deteriorates and ceases to accomplish the watertight sealing. This problem would not arise in the bending device 13 according to the present invention. In the case of the device 13, no adhesive is applied on the abutting surfaces of any operation knob and any lower cover. Rather, it is applied in the gaps between to the projections 325 and the recesses 326 and the gaps between the projection 318 and the recess 319, all of which are located near the fixed shaft 18.

A conventional bending device having a forceps-driving unit is taller than one without a forceps-driving unit. When the bending device is connected to the operation section of an endoscope, it is distant from the hand holding the operation section by the height of the forceps-driving unit. Due to this, the bending device has but poor operability. Since the bending device with a forceps-driving unit and the bending device without a forceps-driving unit differ in height, they cannot use fixed shafts (corresponding to the shaft 18) identical in length. Inevitably, the devices cannot be manufactured at low cost, and the management of their parts is troublesome.

Figure 18:
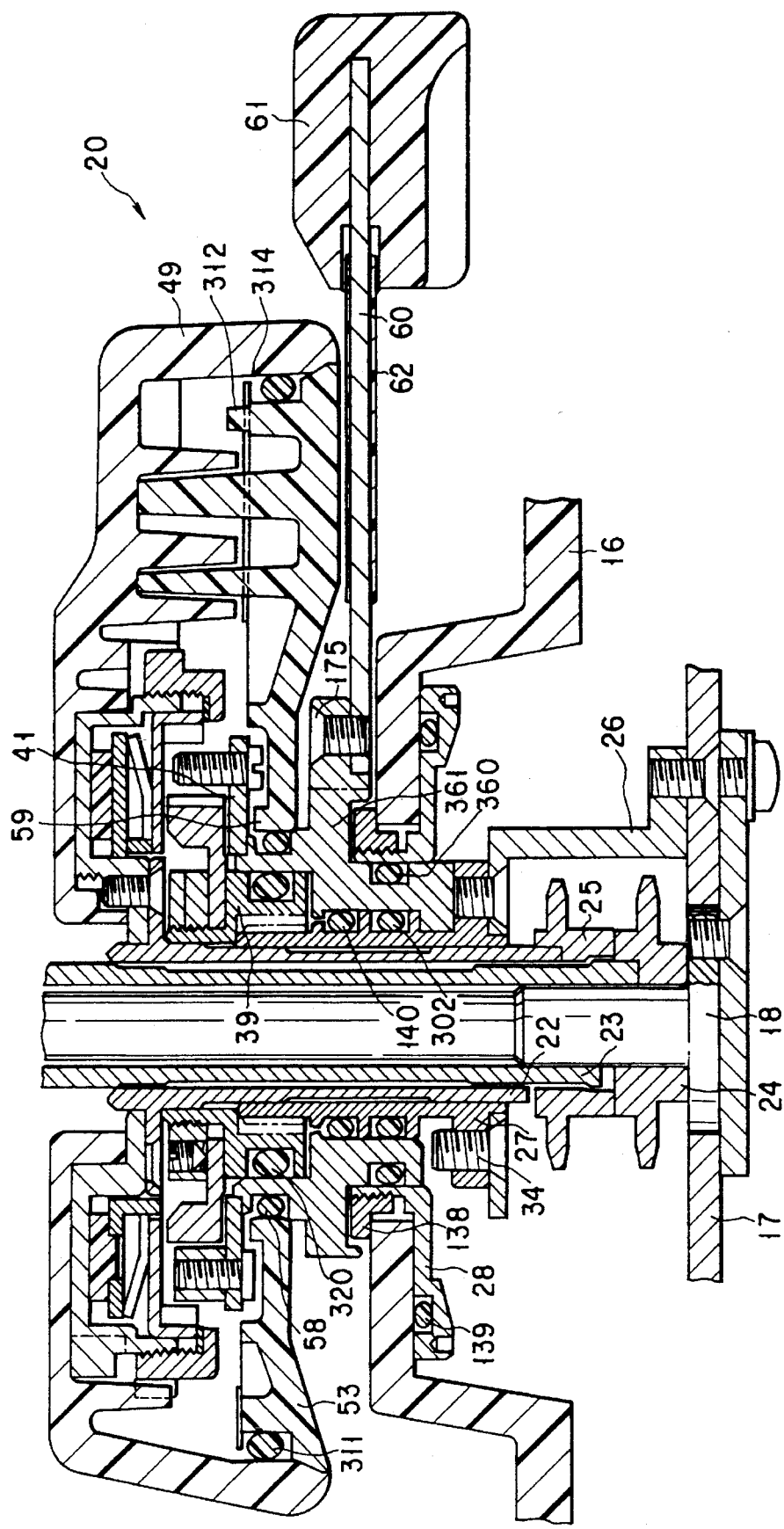
FIG. 18 is a side sectional view of a modification of the first bending unit, which is designed for use in an endoscope which has no forceps-driving unit.

In order to use an identical fixed shaft in both types of bending devices, the device without a forceps-driving unit may be designed as illustrated in FIG. 18. The device of FIG. 18 has a second braking plate 361 which is a combination of a braking plate 56 and a 301, which are identical to those shown in FIG. 4. The second braking plate 361 has its lower end portion mounted on a bearing 27 and fitted in a support shaft 28. It has its upper end portion mounted on a brake shaft 39, fitted in the flange 59 of a first lower cover 53 and set in engagement with a second mount plate 41.

The second braking plate 361 is sealed in watertight fashion from a first bending unit 20 by means of an O-ring 58 and from the support shaft 28 by means of a fourth O-ring 360. Neither a second O-ring 140 nor a third O-ring 302 works as a watertight sealing member. Rather, the O-rings 140 and 302 as members for imparting rotation resistance to the second braking plate 361. Obviously, more sealing members are provided than than in the embodiment described above, in order to prevent the second braking plate 361 from rotating along with the first bending unit 20. Therefore, the second braking plate 361 can be more readily prevented from rotating when an operator rotates the first bending unit 20.

Figure 25:
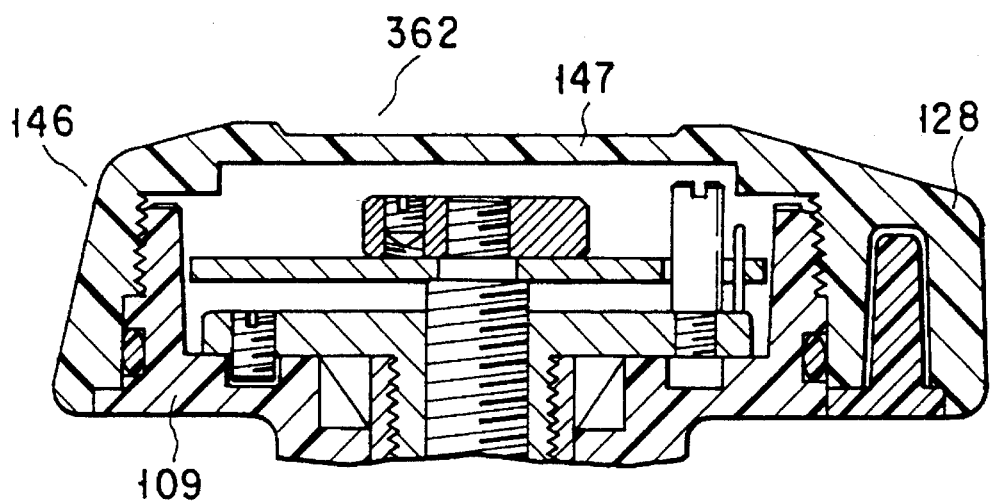
FIG. 25 is a side sectional view of a modification of the third bending unit.

The third operation knob 128 may have a recess 326 in the upper surface as is illustrated in FIG. 25. Due to the recess 326, the thin top wall 147 of the knob 128 remains untouched, exerted with no force, while an operator holds the knob 128 in the hand. The top wall 147 of the knob 128 is therefore less likely to be broken.

Generally, an operator holds the operation section of an endoscope in the left hand and operates the angle knob, the air supply button, the water supply button and the suction button (all mounted on the operation section) with the left hand, while manipulating various levers and buttons with the right hand, thereby twisting, pushing and pulling the insertion section. For an operator whose hands are small it is difficult to reach an RL knob (equivalent to the third operation knob 128 of the embodiment described above). He or she cannot help but pressing the operation section against the breast with the left forearm, so as to turn the RL knob with the left hand. Here arises a problem. As the operation section is pressed against the breast, the RL knob is rotated since its upper surface is not flat or smooth in most case. Consequently, the flexible tube of the insertion section will be bend against the operator's intention. This would never happen with the bending device having the third operation knob 128 shown in FIG. 25, which has a flat and smooth upper surface.

Figure 26:
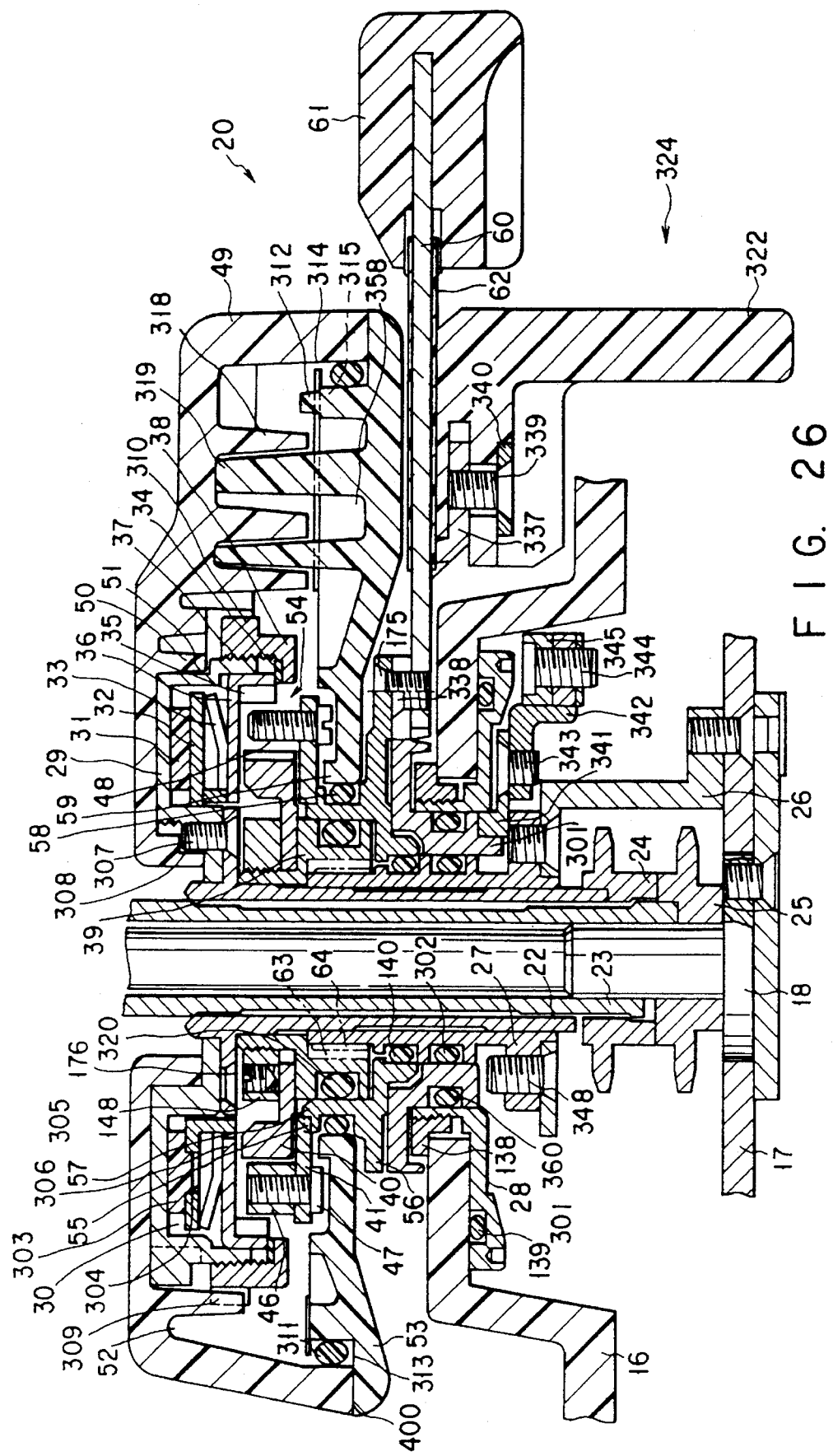
FIG. 26 is a side sectional view of a first modification of the first bending unit.

FIG. 26 is a side sectional view of a first modification of the first bending unit 20. As shown in FIG. 26, the interface 400 between the first lower cover 53 and the first operation knob 49 appears on the circumferential surface of the unit 20, whereas the interface appears on the lower surface of the unit 20 in the embodiment described above. With the first bending unit 20 of FIG. 26 it is easier for an operator to determine whether or not dust and dirt has accumulated at the interface 400 and to remove dust and dirt from the interface 400.

Figure 27:
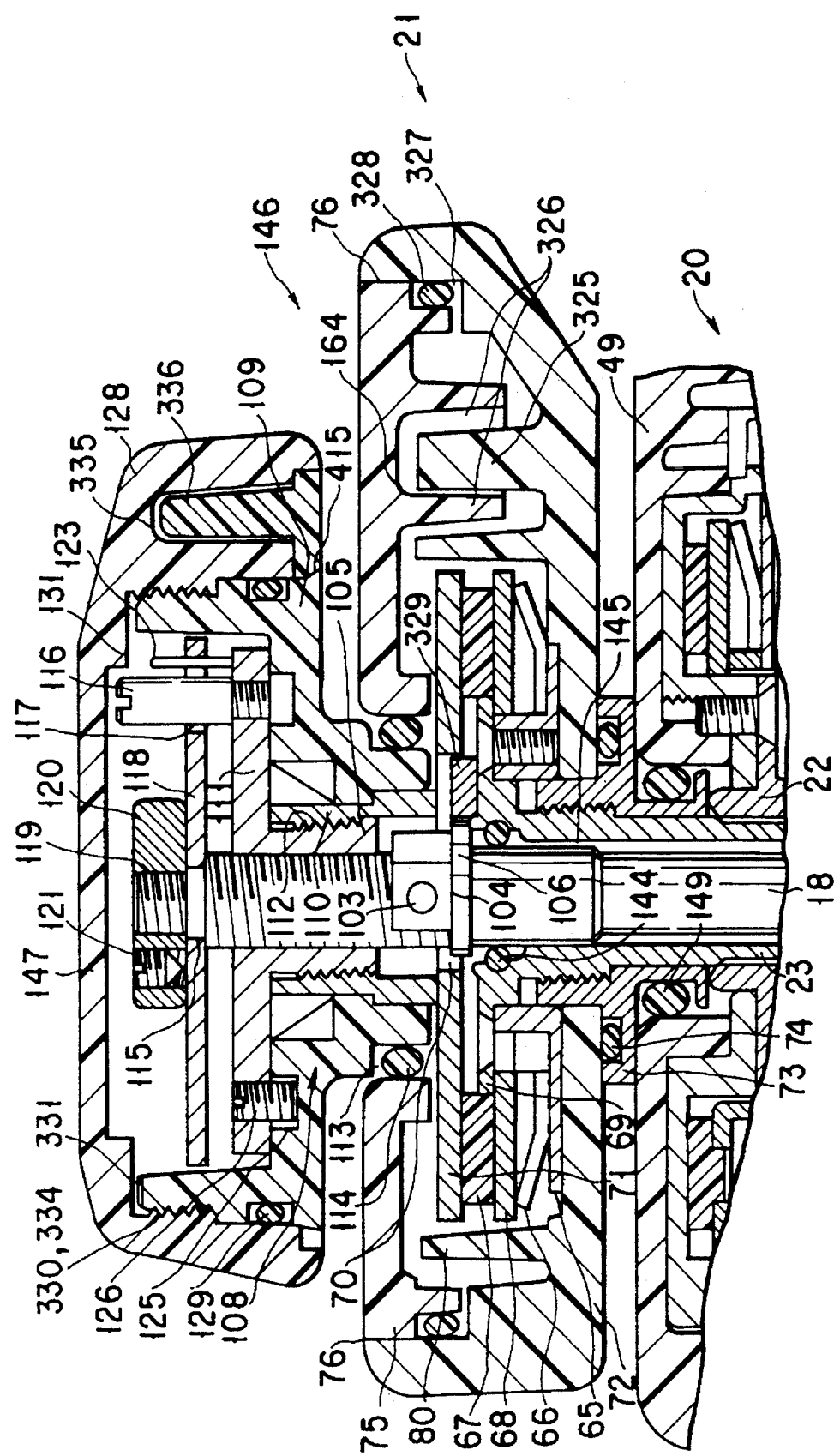
FIG. 27 is a side sectional view of a first modification of the second bending unit.

FIG. 27 is a side sectional view of a first modification of the second bending unit 21, in which the interface 76 between the second lower cover 72 and the second operation knob 75 appears seen on the upper surface of the unit 21. With the second bending unit 21 of FIG. 27 it is easier to determine whether or not dust and dirt has accumulated at the interface 76, by crewing the unit 21 from above, and to remove dust and dirt from the interface 76. The interface 76 opposes the interface 415 between the lower cover 109 and operation knob 147 of the third bending unit 146 and located more outside than the interface 415. Since the interface 76 opposes the interface 415, both the second bending unit 21 and the third bending unit 146 can be washed at a time, merely by applying a washing solution into the gap between the knob 75 of the unit 21 and the lower cover 109 of the unit 146. Labor for washing the sending device 13 can be saved.

Figure 28:
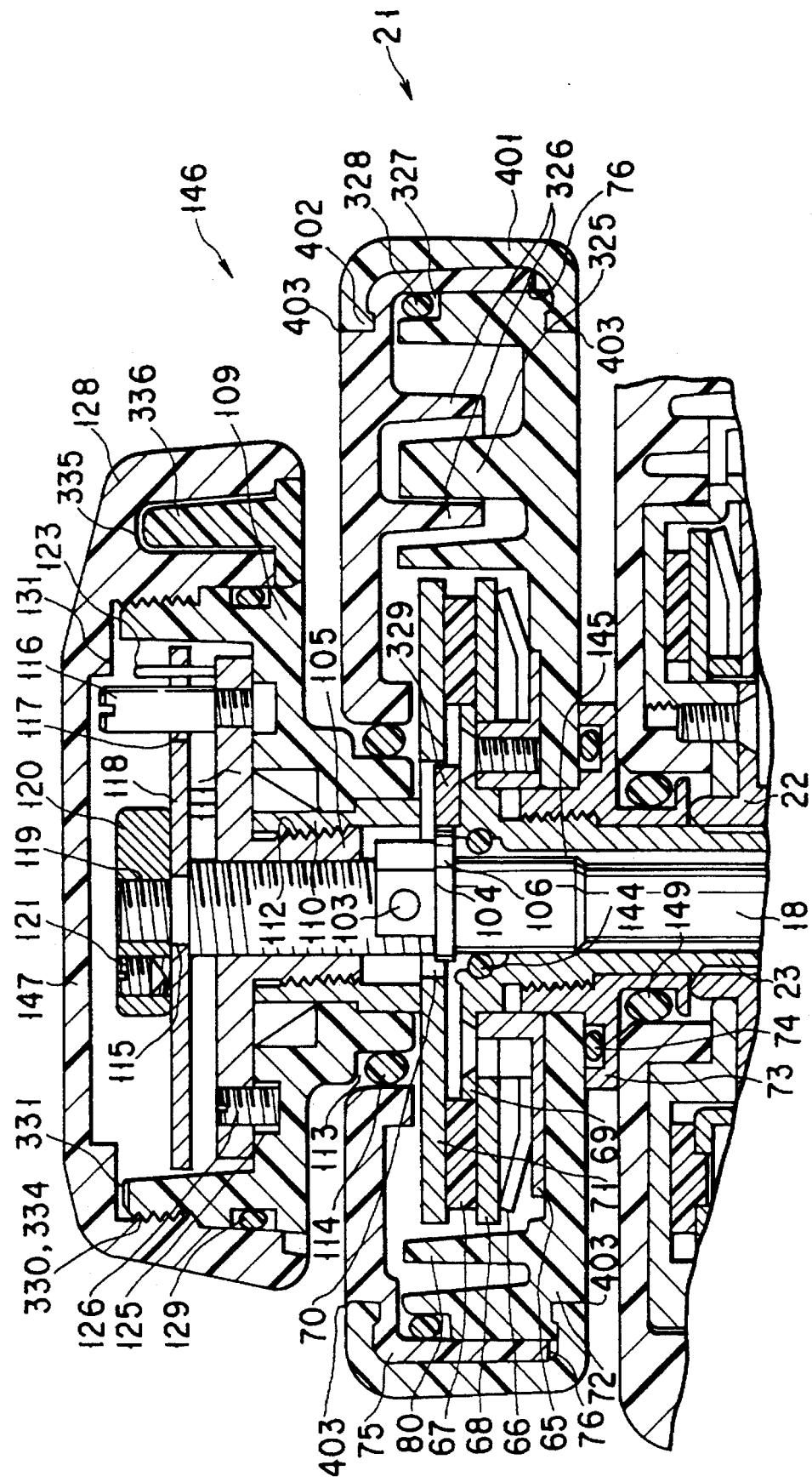
FIG. 28 is a side sectional view of a second modification of the second bending unit.

FIG. 28 is a side sectional view of a second modification of the second bending unit 21. This modified second bending unit has a hollow cylindrical, elastic protective member 401 made of silicone rubber. The member 401 covers the circumferential surfaces of the lower cover 72 and operation knob 75. The member 401 has two annular projections 403 at the upper and lower ends. One of the projections 403 protrudes downwards and fitted in an annular groove cut in the upper surface of the knob 75, and the other projection 403 protrudes upwards and fitted in an annular groove made in the lower surface of the cover 72. The elastic protective member 401 covers the interface 76 between the cover 72 and the knob 75, protecting the interface 76 against an external force. Should the second bending unit 21 be bumped against the floor by mistake, the member 401 would absorb the impact. As a result, the interface 76 would not loosen to form a gap between the lower cover 72 and the operation knob 75. Since the elastic protective member 401 has a smooth outer surface which is continuous to both the lower surface of the cover 72 and the upper surface of the knob 75, the modified second bending unit 21 is easy to wash. In addition, the member 401 serves as a non-skid means, and the modified second bending unit 21 has high operability.

The modified structures described above, with reference to FIGS. 26, 27 and 28 can be equally applied to all bending units 20, 21 and 146.

Figure 29:
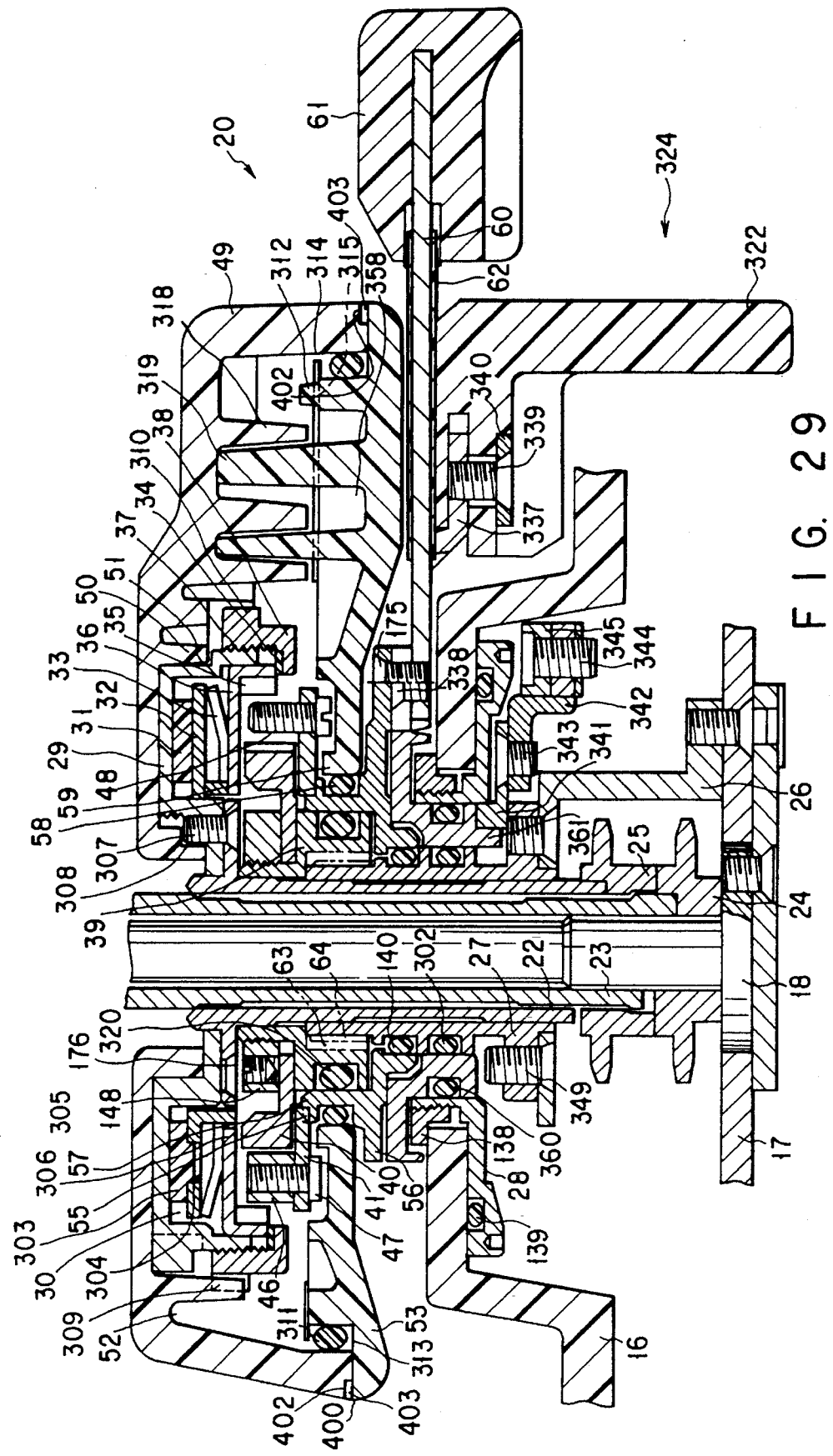
FIG. 29 is a side sectional view of a second modification of the first bending unit.

FIG. 29 is a side sectional view of a second modification of the first bending unit 20. In this modified first bending unit, the interface 400 between the cover 53 and the knob 49 appears on the circumferential surface as in the modified unit 20 shown in FIG. 26. This modified unit has a U groove 402 cut in the interface 400. Adhesive is filled in the U groove 402, reinforcing the connection of the cover 53 and the knob 49. The mass of adhesive has an outer face which is flush with the outer surfaces of the cover 53 and knob 49. The U groove 402 may be replaced by a V groove formed by chamfering the lower edge of the knob 49 or the outer edge of the cover 53, or both.

Since a gap, if any at the interface 400, is filled with the adhesive, neither dust no dirt will accumulate at the interface 400. The structure of FIG. 29 can of course be applied to the second bending unit 21 and the third bending unit 146, as well.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A device to be incorporated in a housing of an operation section of an endoscope, for operating a bending mechanism incorporated in an insertion section of the endoscope, said device comprising:

an operation shaft having:

a distal end portion connected to the bending mechanism, and a proximal end portion projecting from the operation section of the endoscope; and holding means mounted on said distal end portion of said operation shaft for causing rotation of said operation shaft, and said holding means comprising a plurality of covers which are joined together to form a hollow cylindrical member which forms a space around said operation shaft; and wherein said plurality of covers comprise an upper cover and a lower cover which form an outside surface of said hollow cylindrical member of said holding means, and wherein said upper and lower covers abut each other to form an interface on said outside surface.

2. The device according to claim 1, wherein the said plurality of covers are made of electrically insulating material.

3. The device according to claim 1, wherein said interface is located on an outer circumferential surface of said hollow cylindrical member.

4. The device according to claim 1, wherein said interface is located on an upper surface of said hollow cylindrical member.

5. The device according to claim 1, wherein said interface is located on a lower surface of said hollow cylindrical member.

6. The device according to claim 5, wherein said interface opposes a housing of the operation section.

7. The device according to claim 5, wherein said upper cover has an upper surface and an outer circumferential surface which are continuous to each other.

8. The device according to claim 1, further comprising a protective member attached to said holding means and covering said interface.

9. The device according to claim 8, wherein said protective member comprises an elastic member mounted partly on said upper cover and partly on said lower cover.

10. The device according to claim 1, wherein each of said upper cover and said lower cover has a continuous outer surface, and said interface has a surface which is flush with the outer surface of each cover.

11. The device according to claim 10, further comprising adhesive applied to said interface, and said adhesive forming a mass of adhesive having an outer surface which is flush with the outer surface of each cover.

12. The device according to claim 1, wherein each of said upper and lower covers comprises a plurality of projections protruding from an outer circumferential surface thereof.

13. The device according to claim 12, wherein said upper and lower covers comprise screw portions which are set in engagement, aligning the projections of said upper cover with the projections of the lower cover.

14. The device according to claim 12, wherein one of said covers comprises:

an annular seal groove facing the other cover and having a specific cross section; and a seal member having a cross section substantially identical to the cross section of said seal groove and fitted in said seal groove.

15. The device according to claim 1, wherein said seam is sealed.

16. The device according to claim 1, further comprising a seal member interposed between said upper cover and said lower cover, and wherein said upper and lower covers are fastened to each other by adhesive applied inside said seal member.

17. The device according to claim 1, wherein:

one of said covers has a projection;

the other of said covers has a groove filled with adhesive; and said projection is fitted in said groove, whereby said covers are fastened to each other.

18. The device according to claim 1, further comprising a brake mechanism for locking said operation shaft, at least a part of said brake mechanism being located in the space defined by said holding means.

19. The device according to claim 18, wherein said brake mechanism is is arranged to impart a rotation resistance to said operation shaft.

20. The device according to claim 1, further comprising at least one additional holding means for causing a rotation of said operation shaft.

21. The device according to claim 20, wherein said holding means and said at least one additional holding means are spaced apart by a predetermined distance, and said at least one additional holding means has an interface.

22. The device according to claim 21, wherein said interface of said holding means opposes said interface of said at least one additional holding means.

23. The device according to claim 22, wherein said interface of said holding means is displaced with respect to said interface of said at least one additional holding means.

* * * * *

UNITED STATES PATENT AND TRADEMARK OFFICE
CERTIFICATE OF CORRECTION

PATENT NO. : 5,507,717
DATED : April 16, 1996
INVENTOR(S) : KURA et al.

It is certified that error appears in the above-identified patent and that said Letters Patent is hereby corrected as shown below:

```
Title page, Item [56] References Cited,

Under "U.S. PATENT DOCUMENTS" insert:

--5,301,656  4/1994  Negoro  et al
      4,207,873  6/1980  Kruy
      5,007,406  4/1991  Takahashi et al
      5,014,685  5/1991  Takahashi--.

Under "FOREIGN PATENT DOCUMENTS" insert:

--63-9282  3/1988  Japan--.
```

Signed and Sealed this

Twenty-ninth Day of September, 1998

Attest:

BRUCE LEHMAN

*Attesting Officer*     *Commissioner of Patents and Trademarks*